United States Patent [19]

Ryner et al.

[11] Patent Number: 5,753,434
[45] Date of Patent: May 19, 1998

[54] METHODS AND COMPOSITIONS FOR ALTERING SEXUAL BEHAVIOR

[75] Inventors: Lisa C. Ryner, Woodside; Bruce S. Baker, Stanford, both of Calif.; Steven A. Wasserman; Diego H. Castrillon, both of Dallas, Tex.

[73] Assignee: The Board of Trustees of the Leland Stanford Junior University, Stanford, Calif.

[21] Appl. No.: 386,495

[22] Filed: Feb. 10, 1995

[51] Int. Cl.⁶ ............... C12Q 1/68; C12N 15/85; C12N 5/10; C12N 15/12
[52] U.S. Cl. ............... 435/6; 435/69.1; 435/70.1; 435/91.1; 435/172.3; 435/240.2; 435/320.1; 536/23.5; 536/24.1; 536/24.31
[58] Field of Search ................. 435/6, 69.1, 91.1, 435/172.3, 70.1, 240.2, 320.1; 935/9, 34, 76; 536/23.5, 24.31, 24.1

[56] References Cited

PUBLICATIONS

T. Ramseir –Database listing –STN Biosis AN 94:17067, criing J. Mol. Biology 234(1) ('93) 28–44.

T. Ramseier et al. Database Listing : STN/Biosis AN 93:358066 criing Abstr. Gen. Mat. Am. Soc. Microbiol 93(0) ('93) 225.

L. Maher III, BioEssays, 14 (12) (Dec. 92) 807–15.

Ryner, L., et al., "Hormones and Receptors/Sex Determination," 35th Annual Drosophila Conference, Apr. 20–24, 1994 (Chicago, IL) [Program and Abstracts Volume], p. 32.

Taylor, B.J., et al., "Behavioral and Neurobiological Implications of Sex–Determining Factors in Drosophila," Developmental Genetics 15:275–296 (1994).

Gailey, D.A., et al., "Elements of the fruitless locus regulate development of the muscle of Lawrence, a male-specific structure in the abdomen of *Drosophila melanogaster* adults," Development L13, 879–890.

Gailey, D.A., et al., "Behavior and Cytogenetics of fruitless in *Drosophila melanogaster*: Different Courtship Defects Caused by Separate, Closely Linked Lesions," Genetics 121: 773–785 (Apr. 1989).

Zollman, S., et al., "The BTB domain, found primarily in zinc finger proteins, defines an evolutionarily conserved family that includes several developmntally regulated genes in Drosophila," Proc. Natl. Acad. Sci. USA, 91: 10717–10721 (Oct. 1994).

*Primary Examiner*—Charles C. P. Rories
*Attorney, Agent, or Firm*—Charles K. Sholtz; Peter J. Dehlinger

[57] ABSTRACT

Methods and compositions effective to alter the sexual or reproductive behavior of an insect are disclosed. The compositions include polynucleotides and polypeptides corresponding to the fru gene in Drosophila and its homologs in other species. Methods of identifying a compound effective to alter the reproductive behavior of an insect are also disclosed.

14 Claims, 11 Drawing Sheets

EcoRI

GAATTCGAGGACGTGTGACGATGGAGCAACCCTTCCCCCCAGA

TCGAAAGAGAATA TCATCAATCAACA TTCCCGTGCCCGGAGGAG

CTGC TCTTCAATCAACA CTCAACCCGACTGGGCCCTCAAAAGC

CCGGCAACCTAAAGTTAGTCTTTCATTAGCCTCTTCTATCAATT

AGTTAGTCAGCCAACGTTTCTCTCTCTCATAATTCTAACCGA

AAGTAAGCATAGAAAGAACCAAT ACTTCAATCAACA TACCCAC

AAAAAAAAACAAATCCCCACCAACTGGCGTCGGTAAGTGAAGAG

CCATTTAATTATAGNNNNNNNNNNNNNNNNNNNNNNNNNNNNN

NNNNNNNNNNNNNNNNNNNNNNNNNNNNNNNNNNNNNNNNNNN

NNNNNNNNNNNNNNNNNNNNNNNNNTGATCGCCGATGATGCATGT

GATAAGCAAGTGATGAACAATCGTAGCAATCAGGCAGTAGGNN

NCTTGAACAAATTTAACTTAGCTGNATTTTGCGCATGCCAAATG

AAAAATAACAAACCGTAAATTCCAATGGTAACTAAAACTAGCAA

TACTAACTCTAGCCGATGGAACATGCAACCGAATTC

EcoRI

Fig. 4

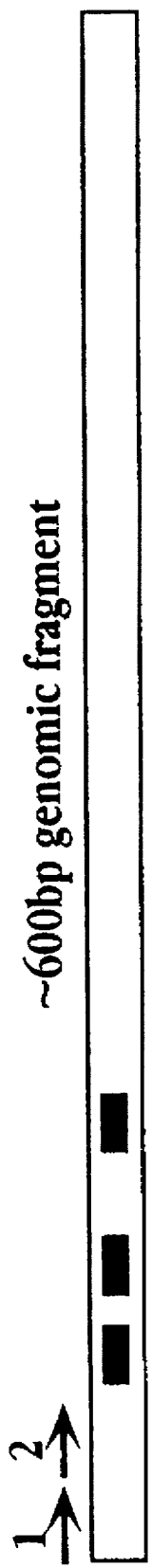
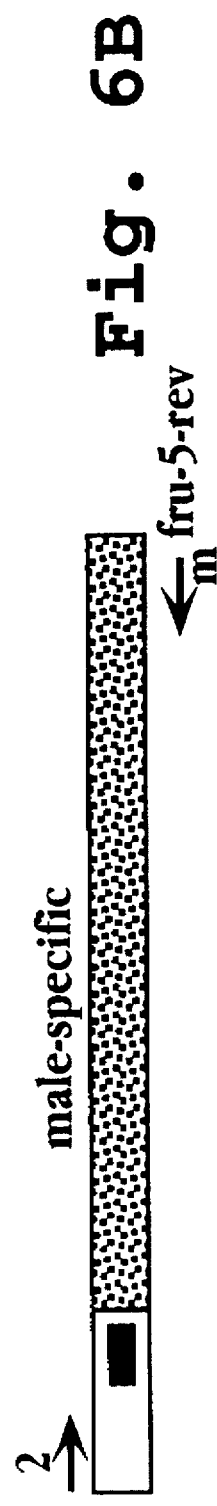
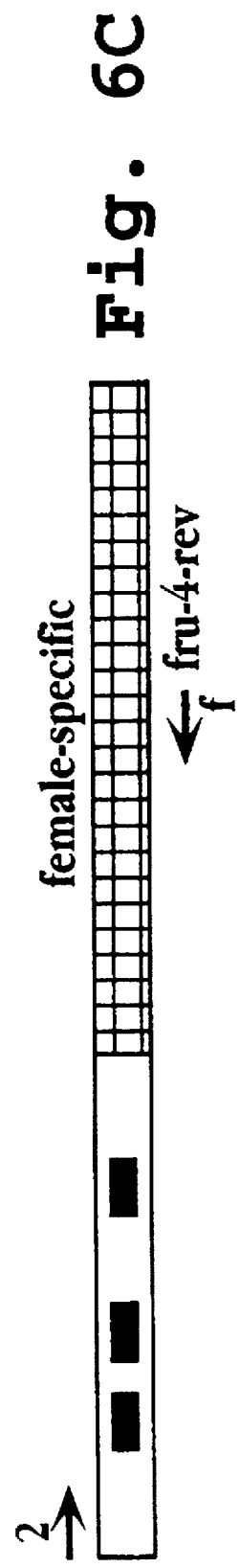
3' RACE products:

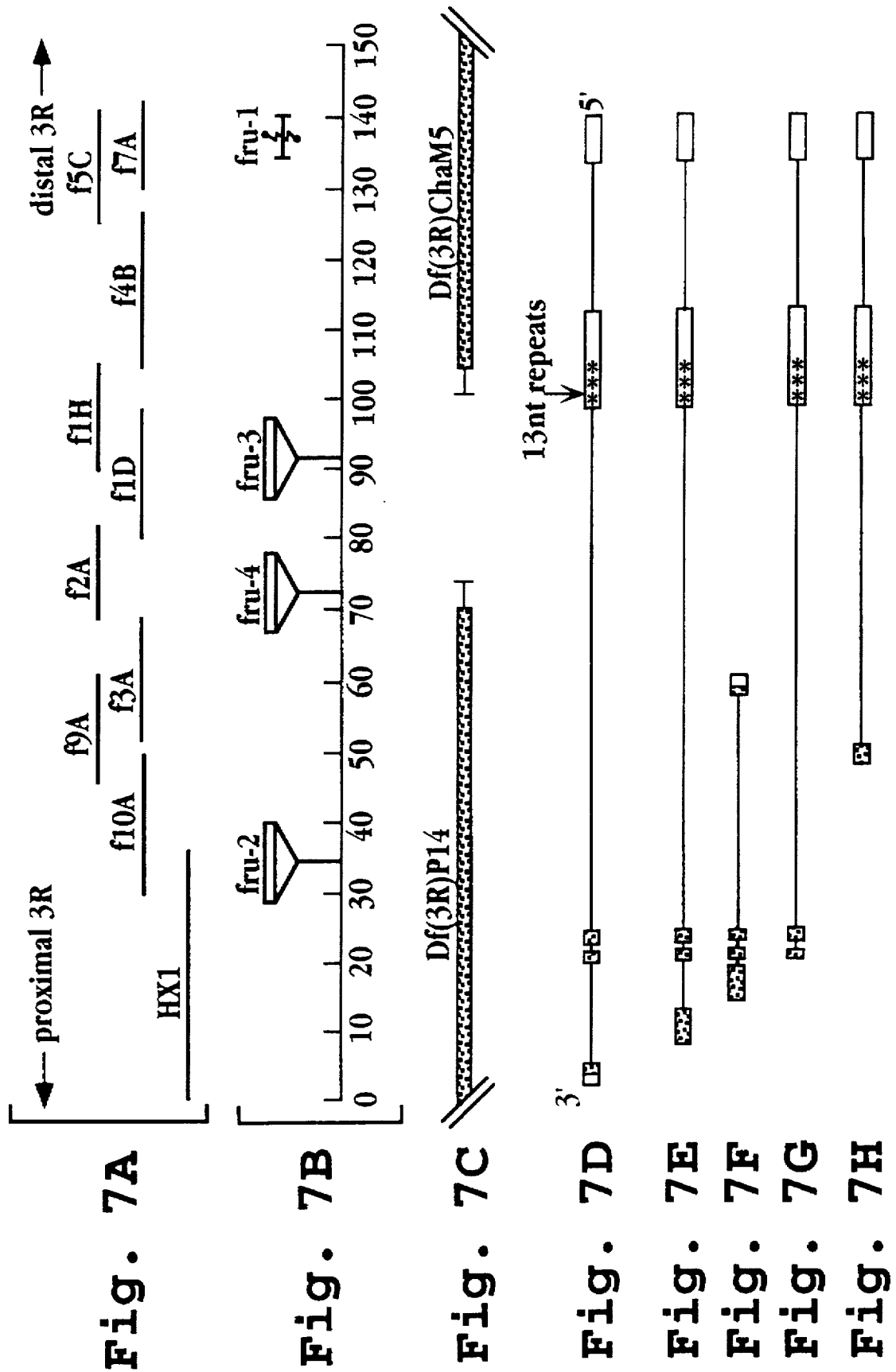

```
gaattcggcacgagattcacctatggcatatcatcagcaacacatcaacgcactcctctgctatgtctgcaatcaacc
aaatatcaactattacgcccaaagtaaacgtagatcaacgtcaacatcaattttaaagttttacgttggttgttcgaaagagtttaa
atgcccttaaactattacgcccaaagtaaacgtagatcaaacgtagattaaagtaatattagccaatcaatcgtaaaatatcagctttcg
tttttaaaacttaccaaagtgacttgtccatcaattgcaaatctaaagttaactactacaatagaatacgtattcttgtttcttcgc
atatcactaaccaaagtgtttgccacgagtgtattaaaatgttaactactacaatagaatacgtattcttgtttcttcgc
tagtatgtatagcaaactgcaagaaacaaccaactaattaatatttaatagcataatgtaatatcgtaagaa
tatcatagatttaaggcagagcatttcagacagcacttgtaccgttctagacttaagtattcgaagtatacgtaactcaa
gcaatccaataacaataagtagaagtcttcaaaatactatacacgaatcctcagtcaaaccctacaa
tattacttagataaacatataqtattatagccaaagtccaggaaaggagttgtaagccattgcatatatatattggta
gataaagaacagctaacgaaagggtccacagtctacccatcaaagtacttagaataactagaccaagaagta
gatatctatatatatcgagttctgctaacatcaaagcaatattacaagttaacgcaactaaaacacacactagccaagaagta
acactcttcaaagcaatacccatagtagtcctaagtcctaqgcataaaccqcqaqcaccacqcqqataatqatqccacccatctagtqtaccccatctagtgtagtcqctaaqt
attaatttaccaagagtacaaactgtaaagqaacccctattqaagtqaqcaaacaqatqaaqcqaaqcaatqaqcaaataqaqqaqcaatqtqaaqaatttcqaqqac
gtgtgacgatggagcaacactcaacctgaaagtagtcgcaagctggaactqtqaaaqccqqcqaaccqqcqccaatcqaaqcccqqctaaqccaatactaqctqaactaqaattcqaqqactaqaqtqacqaccaqccqcaccaatccqccqqctaaqccaatataqc
tcttcaatcaacactcaacctqqqqccctcaaaaaqcccqqcaacctaaaqttaqtcttttcattaqctctctatcaatactqctctaa
caattagttagtcagccaacgtttctctctcataataacaaatcccaccaactgcgcqqtacaacctqaccqqcqctaqaaqcataqaaaqcataqaaqcataqaaqcataaataqctqaa
tcaacataccacacaaaaaacaaatcccaccaactgcgcqqtacaacctqaccqqcqctaqaaqcataqaaaqcataqaaqcataqaaqcataaataqctqaa
CTGCTTGCGCTGAACAATCATCCCACAAATTTGACCGGCGTGCTAACCTTCACTGCTGCAGCGGAGGCGCTATGCGACG
```

```
ACTCGTCCATTTAAgggcgtgtggccgggcccaagtgcagcccatcaccgcccagcttaccagcagccgcat
cataagcagaagcagaagcagcagcaacagcagcagcatcagccgcagcagcagcagcagcaacagccagc
ttactacgtcagcaactatacagcaacatacagcaatatagatacagcgatagtttattgtaaatcgctgcagttc
tagtggattttcttgcattagtcgtcgtcccagtcgtgtacattaccccactagctatccaagcaataaccataaccca
aactagtagaaaaccgaagatgctatgctgcaaaacgtaaacacaagtatattgataatcttaactaaa
cttattgataaactttgacacaatcgtcccatcatcgtcccagcatagagggccagtgcggaggcgaaattaggaaaaggtttcagt
tgcgagtcgagagaggatatgcccagcatagagggccagtgggaggcggaataactataaaagttttccaaagccacaacaaacc
gtttcgaagtttcctaaatgttgtttcctaaaactatactactagagagagaaagtcgagga
aatcgtttgagccgattcagcaaattgggtcactaccacacgcgggtcagcagcagcagtcaccacaa
aatgaggatgcggatgcgaatgcgaaggtcacattaggtttagttttactttaattgtctagatttttagtgttaaccgatatgt
atactactcatacgaaggtcacattaggtttagttttacttcaactacaaagaaatttcatatacctcaaatgcattcagtttt
tctgcggagtaggaaacggagggctactactacgtagtcagttagcatcagttagccacatcaaagtaccacatacatatatgttattttt
attgttgattgcttttaatttagtcgtctacgtagtcagttagccaatagtttaccagtttcctcgtttttttagtgtgtggtgt
taatcggttccaattttgaatcggcgagatagccaatagtttacccagtttcctcgttttttagttacgtccgaacacttgaacca
tccctatcactatcactttttgattttgttatttttatatttattgtcacacgtttattcactgtaaagtacacactaaacacat
cctcacttttttgttaagcttgtttataatttatatttatgtcacacgtttattagtaaagtacactaaacacat
atgaaatcacgcggaagaaagttagttgatatgag
```

Fig. 9C

METHODS AND COMPOSITIONS FOR ALTERING SEXUAL BEHAVIOR

This work was supported in part by NIH Grant NS33352-01. Accordingly, the United States Government has certain rights in this invention.

FIELD OF THE INVENTION

This invention relates to methods and compositions for altering sexual behavior, particularly sexual behavior affected by the fruitless gene of Drosophila and its homologues in other species. More specifically, the invention relates to methods and compositions employing the fruitless gene and its products and phenotypes, for insect pest control.

REFERENCES

Ashburner, M., DROSOPHILA: A LABORATORY MANUAL, Cold Spring Harbor Laboratory (Cold Spring Harbor, N.Y.) (1989).

Ausubel, F. M., et al., CURRENT PROTOCOLS IN MOLECULAR BIOLOGY, John Wiley and Sons, Inc., Media PA.

Baker, B. S., Nature 340:521–524 (1989).

Bartel, P., et al., BioTechniques 14:920–924 (1993).

Belote, J. M., and Baker, B. S., Proc. Nat. Acad. Sci. USA 84:8026–8030 (1987).

Boggs, R. T., et al., Cell 50:739–747 (1987).

Brent, R., et al., Cell, 43:729–736 (1985).

Bridges, C. B., Science 54:252–254 (1921).

Burtis, K. C., and Baker, B. S., Cell 56:997–1010 (1989).

Burtis, K. C., et al., EMBO J. 10:2577–2582 (1991).

Calkins, C. O., et al., Florida Entomologist 71:346 (1988).

Chien, C.-t, et al., Proc. Natl. Acad. Sci. U.S.A., 88:9578 (1991).

Cline, T. W., in EVOLUTIONARY MECHANISMS IN SEX DETERMINATION, (Wachtel, S.S., Ed.), CRC Press, Cleveland, Ohio, pp. 23–36 (1988).

DiAntonio, et al., J. Neuroscience 13:4924 (1993).

Durfee, T., et al., Genes & Development 7:555 (1993).

Fields, S., et al., Nature 340:245 (1989).

Frohman, M. A., et al., Proc. Natl. Acad. Sci. U.S.A 85:8998 (1988).

Frohman, M. A., in PCR PROTOCOLS (Innis, M. A., et al., Eds.) Academic Press, San Diego, Calif., pp. 28–38 (1990).

Giebultowicz, J. M., and Truman, J. W., J. Comp. Neurol. 226:87–95 (1984).

Gyuris J., et al., Cell, 75:791–803 (1993).

Harlow, E., et al., ANTIBODIES: A LABORATORY MANUAL, Cold Spring Harbor Press (1988).

Harry, J. L., et al., Genetica 87:114 6 (1992).

Hedley, M. L., and Maniatis, T., Cell 65:579586 (1992).

Hodgkin, J., Nature 344:721–728 (1990).

Hoshijima, K., et al., Science 252:833–836 (1991).

Lawrence, P. A., and Johnston, P., Cell 45:505–513 (1986).

Lucchesi, J. C., and Manning, J. E., Adv. Genet. 24:371–429 (1987).

Maniatis, T., et al., Cell 19:687–701 (1978).

Matsumoto, S. G., and Hildebrand, J. G., Proc. Roy. Soc. Lond. B 213:249–277 (1981).

McKeown, M., and Madigan, S. J., Curr. Opin. Cell Biol. 4:948–954 (1992).

Miller, et al., Science 237:775 (1987).

Moses, et al., Nature 340:531 (1989).

Mullis, K. B., et al., U.S. Pat. No. 4,683,195, issued 28 Jul. 1987.

Mullis, K. B., U.S. Pat. No. 4,683,202, issued Jul. 28, 1987.

Nagoshi, R. N., et al., Cell 53:229–236 (1988).

Possidente, D. R., and Murphey, R. K., Devel. Biol. 132:448–457 (1989).

Ryner, L. C., and Baker, B. S., Genes Devel. 5:2071–2085 (1991).

Sambrook, J., et al., MOLECULAR CLONING: A LABORATORY MANUAL, Second Edition, Cold Spring Harbor Laboratory (Cold Spring Harbor, N.Y.) (1989).

Sanger, F., et al., PNAS 74:5463–67 (1977).

Schneider, I., J. Embryol. Exp. Morphol. 27:353 (1972).

Siegel, R. W., et al., Behav. Genet. 14:383–410 (1984).

Slee, R., and Bownes, M., Quart. Rev. Biol. 65:175–204 (1990).

Smith, D. B., et al., Gene 67:31 (1988).

Speith, H. T., Ann. Rev. Entomol. 19:385 (1974).

Stocker, R. F., and Gendre, N., Devel. Biol. 127:12–24 (1988).

Taylor, B. J., Genetics 132:179–191 (1992).

Taylor, B. J., J. Neurogenet. 5:173–192 (1989a).

Taylor, B. J., J. Neurogenet. 5:193–213 (1989b).

Taylor, B. J., J. Neurogenet. 8:251 (abstract) (1993).

Taylor, B. J., and Truman, J. W., Development 114:625–642 (1992).

Technau, G. M., J. Neurogenet. 1:113–126 (1984).

Thorn, R. S., and Truman, J. W., J. Comp. Neurol. 184:489–503 (1989).

Wolfner, M. F., Trends Genet. 4:333–337 (1988).

Wong, T. T. Y., et al., J. Econ. Entomol. 85:1671 (1992).

Yang, X., et al., Science 257:680 (1992).

Zollman, S., et al., PNAS 91:10717 (1994).

BACKGROUND OF THE INVENTION

Insect pests account for massive economic losses in agriculture, and pose health risks to millions of individuals. Traditional strategies for control of insects include chemical and biological approaches. Chemical approaches typically employ any of a variety of pesticides, each with varying degrees of toxicity to non-insect animals. Biological approaches typically utilize naturally-occurring organisms pathogenic to insects or the development of crops that are more resistant to insects.

With an increased understanding of the mechanisms underlying insect behavior, and how these mechanisms relate to similar processes in other animals, it has become possible to develop hybrid approaches to insect pest control. One type of hybrid approach involves the release of sterile individuals into the environment. Such sterile release programs have been successful at significantly reducing insect populations (see, for example, Wong, et al., and Calkins, et al.).

SUMMARY OF THE INVENTION

In one aspect, the invention includes a substantially isolated FRU polynucleotide. In one embodiment, the polynucleotide is highly homologous to a polynucleotide derived from an insect belonging to the phylum Arthropoda. In another embodiment, the polynucleotide is highly homologous to a polynucleotide derived from an insect belonging the order Diptera. In a related embodiment, the polynucleotide is highly homologous to a polynucleotide derived from an insect selected from the group consisting of medfly, fruit fly (e.g., Drosophila), tse-tse fly, sand fly, blowfly, flesh fly, face fly, housefly, screw worm-fly, stable fly, mosquito, and northern cattle grub. In another related embodiment, the polynucleotide contains the sequence represented as SEQ ID NO:9. In another embodiment, the polynucleotide encodes a FRU polypeptide having the sequence represented as SEQ ID NO:10.

In a related aspect, the invention includes a substantially isolated FRU polypeptide. In one embodiment, the polypeptide is highly homologous to a polypeptide derived from an insect belonging to the phylum Arthropoda. In another embodiment, the polypeptide is highly homologous to a polypeptide derived from an insect belonging the order Diptera. In a related embodiment, the polypeptide is highly homologous to a polypeptide derived from an insect selected from the group consisting of medfly, fruit fly (e.g., Drosophila), tse-tse fly, sand fly, blowfly, flesh fly, face fly, housefly, screw worm-fly, stable fly, mosquito, and northern cattle grub. In another related embodiment, the polypeptide contains the sequence represented as SEQ ID NO:10.

In another aspect, the present invention includes an expression system and a method of producing a FRU polypeptide. The method includes introducing into a suitable host a recombinant expression system containing a FRU polynucleotide having an open reading frame (ORF), where the ORF has a polynucleotide sequence which encodes a FRU polypeptide, and wherein the ORF is operably linked to a control sequence which is compatible with a desired host. The vector is designed to express the FRU polypeptide in the selected host when the host is cultured under conditions resulting in the expression of the ORF sequence. A number of expression systems can be employed, including insect expression vectors such as baclovirus vectors, a lambda gt11 expression system with an Escherichia coli host, and other yeast, mammalian cell and bacterial expression vectors.

The expressed FRU protein may be isolated by a variety of known methods, depending on the expression system employed. For example, a beta-gal-FRU fusion protein may be isolated by standard affinity methods employing an anti-beta-gal antibody. The FRU polynucleotide sequence may be modified so as to result in the expression of a mutant polypeptide (fru) which may give rise to a dominant mutant phenotype when expressed in an insect host. Mutants generated as described above may be used to generate transgenic insects with altered sexual or reproductive behavior (e.g., sterile insects useful for insect control).

In yet another aspect, the present invention includes both polyclonal and monoclonal antibodies directed against FRU epitopes, or against epitopes encoded by a portion of the sequence presented as SEQ ID NO:9. Such antibodies may be used in co-immuneprecipitation methods to identify proteins and/or nucleic acids that interact with the FRU protein and are involved in controlling sexual behavior. The antibodies may also be used to identify target genes whose transcription is regulated by FRU polypeptide. Once identified, the regulatory regions of the genes may be incorporated into reporter constructs and used to screen for compounds which inhibit the interaction of the FRU polypeptide with the regulatory sequences. Such compounds may be useful as insect control agents.

Also included in the invention is a method of identifying a compound effective to alter the reproductive behavior of a target insect. The method includes (i) treating an insect cell, obtained from a target insect and carrying an expression vector containing FRU regulatory sequences operably linked to a reporter gene, with a test compound, (ii) evaluating the level of expression of the reporter gene in the treated cell, and (iii) identifying the compound as effective if the compound significantly decreases the expression of the reporter gene in the treated cell relative to the expression of the reporter gene in untreated cells carrying the expression vector.

In one embodiment, the target insect belongs to the phylum Arthropoda. In another embodiment, the target insect belongs to the order Diptera. In a related embodiment, the target insect is selected from the group consisting of medfly, fruit fly (e.g., Drosophila), tse-tse fly, sand fly, blowfly, flesh fly, face fly, housefly, screw worm-fly, stable fly, mosquito, and northern cattle grub. In another embodiment, the insect is a Drosophila species, and the cells are selected from the group consisting of Schneider's Line 2 and Drosophila Kc cells. In one embodiment, the reporter gene encodes a protein selected from the group consisting of chloramphenicol acetyl-transferase (CAT), β-galactosidase (β-gal) and luciferase.

These and other objects and features of the invention will become more fully apparent when the following detailed description is read in conjunction with the accompanying drawings.

BRIEF DESCRIPTION OF THE FIGURES

FIG. 4 presents the partial nucleotide sequence of a ~600 bp EcoRI DNA fragment isolated from clone λCh4A-11.

(FIG. 5A) or 65° C. (FIG. 5B).

FIG. 6A shows a schematic of the ~600 bp EcoRI genomic DNA fragment shown in FIG. 4, indicating the positions of primers fru-1 (1) and fru-2 (2).

FIG. 6B shows a schematic of a male-specific 3'RACE product, indicating the positions of primers fru-2 (2) and fru-5-rev.

FIG. 6C shows a schematic of a female-specific 3'RACE product, indicating the positions of primers fru-2 (2) and fru-4-rev.

FIG. 7A shows a schematic of the DNA fragments (f10A, f9A, f3A, f2A, f1D, f1H, f4B, f5C and f7A) isolated as part of a genomic walk spanning the fru locus at position 91B of the third chromosome, as well as a schematic of the location of the HX1 cosmid, relative to the map of the 91B region shown in FIG. 7B.

FIG. 7B shows a schematic of the 91B region of chromosome 3, indicating the positions of know fru lesions (mutants fru-2, fru-4, fru-3 and fru-1).

5

FIG. 7C shows a schematic of two fru deficiencies, Df(3R)P14 and Df(3R)ChaM5, relative to the map of the 91B region shown in FIG. 7B.

FIGS. 7D, 7E, 7F, 7G and 7H show schematic diagrams of the location of sequences comprising five fru cDNA transcripts relative to the map of the 91B region shown in FIG. 7B. Exons are indicated as boxes and introns as lines.

Figure 8:
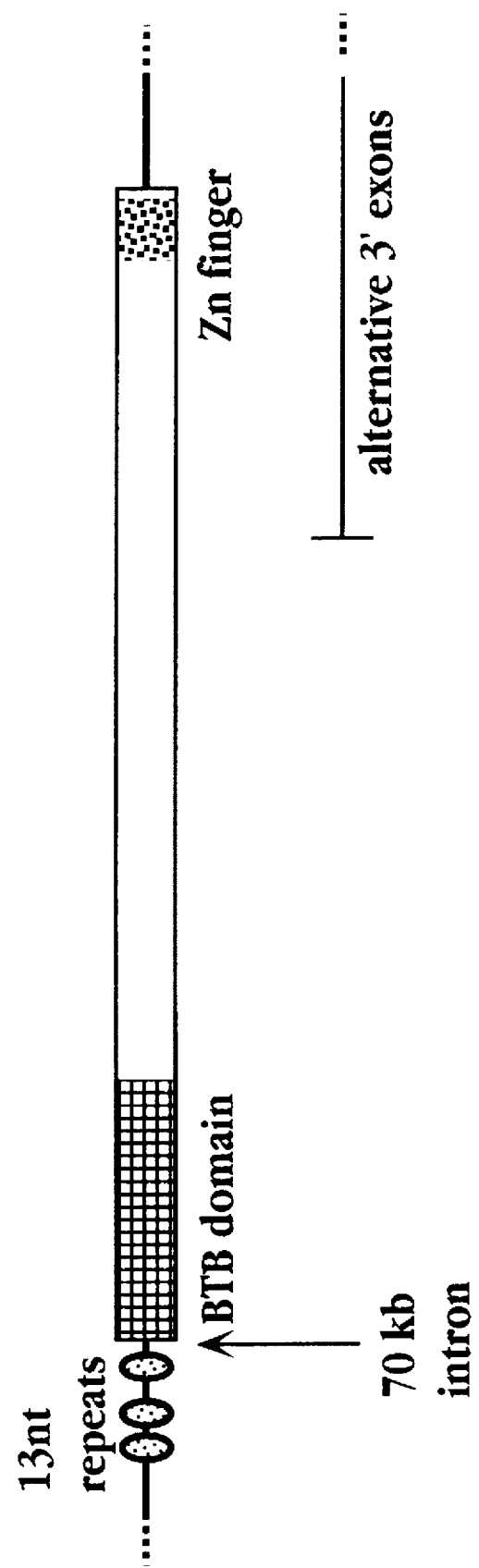

FIG. 8 shows a schematic of the polypeptide predicted from the sequence (SEQ ID NO:9) of the transcript (Fru#1) schematized in FIG. 7D.

Figure 9B:
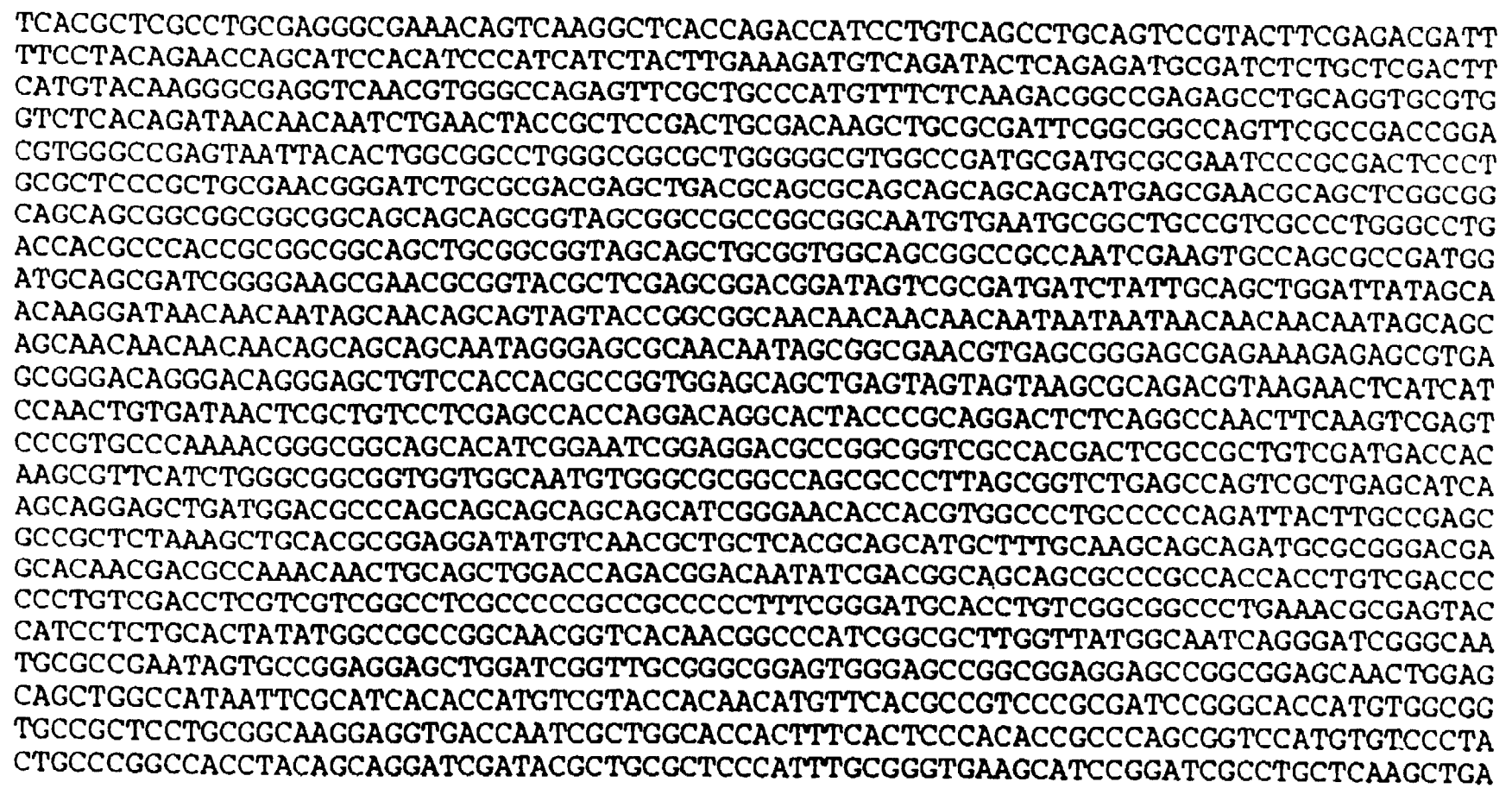

FIG. 9A, 9B and 9C shows the DNA sequence (SEQ ID NO:9) of the transcript (Fru#1) schematized in FIG. 7D.

BRIEF DESCRIPTION OF THE SEQUENCES

SEQ ID NO:1 is the nucleotide sequence of the 3× dsx repeat DNA probe.

SEQ ID NO:2 is the nucleotide sequence of the sense dsx repeat 21-mer oligonucleotide.

SEQ ID NO:3 is the nucleotide sequence of the antisense dsx repeat 21-mer oligonucleotide.

SEQ ID NO:4 is the nucleotide sequence of the −20 sequencing primer.

SEQ ID NO:5 is the nucleotide sequence of the fru-1 primer.

SEQ ID NO:6 is the nucleotide sequence of the fru-2 primer.

SEQ ID NO:7 is the nucleotide sequence of the fru-5-rev primer.

SEQ ID NO:8 is the nucleotide sequence of the fru-4-rev primer.

SEQ ID NO:9 is the nucleotide sequence of the Fru#1 cDNA transcript.

SEQ ID NO:10 is the translated amino acid sequence of SEQ ID NO:9.

SEQ ID NO:11 is the nucleotide sequence of the ~600 bp EcoRI fru genomic clone insert containing 3 dsx repeats.

DETAILED DESCRIPTION OF THE INVENTION

Definitions

A FRU polynucleotide is defined herein as a polynucleotide that selectively hybridizes with a probe directed to unique sequences in the fru polynucleotides presented herein (e.g., SEQ ID NO:9, SEQ ID NO:11). Such unique sequences are sequences that do not overlap common regions of other transcription factors, such as the BTB region and zinc (Zn) finger domains. For example, a probe containing the sequence between positions 1870 and 2080 of SEQ ID NO:9 is directed to unique sequences in the fru polynucleotides presented herein.

A FRU polypeptide is defined herein as a polypeptide encoded by the open reading frame of a FRU polynucleotide.

Regulatory sequences, or control sequences, refer to specific sequences at the 5'and 3'ends of eukaryotic genes which may be involved in the control of transcription. For example, most eukaryotic genes have an AT-rich region located approximately 25 to 30 bases upstream from the site where transcription initiation site. Similarly, most eukaryotic genes have a CXCAAT region (X may be any nucleotide) 70 to 80 bases upstream from the start of transcription.

The term "operably linked", as used herein, denotes a relationship between a regulatory region (typically a promoter element, but may include an enhancer element) and the coding region of a gene, whereby the transcription of the coding region is under the control of the regulatory region.

A polynucleotide or polypeptide is "derived from" a particular organism if that polynucleotide or polypeptide was originally isolated from that organism. For example, a polynucleotide in a plasmid propagated in *E. coli* is derived from Drosophila if that polynucleotide was originally isolated from Drosophila mRNA, genomic DNA or cDNA. Alternatively, a polynucleotide or polypeptide is "derived from" a particular organism if the sequence of that polynucleotide or polypeptide is based on the sequence of the corresponding sequence from that organism. For example, a polypeptide is derived from Drosophila if the sequence of the polypeptide is the same as the sequence of the corresponding native Drosophila polypeptide.

I. Overview of the Invention

In the fruit fly *Drosophila melanogaster*, as in other animals, one of the most obvious differences between adults of different sexes are the sex-specific behaviors involved in reproduction. In flies, reproductive behaviors for males include the detection of females, precopulatory courtship, and finally copulation (for review: Speith, 1974).

Many aspects of reproductive behavior are controlled by the central nervous system (CNS), and may accordingly have a neuronal cell basis. Sexually dimorphic neurons in the CNS are intimately associated with the performance of sex-specific behaviors. In the nervous system, neuronal differences may be manifested in a variety of ways. Neurons may be unique to one sex, or neurons may be present in both sexes but differ in size, shape, anatomical connections, or physiology.

In insects, a variety of sex-specific differences in the CNS have been described both in the sensory integration and in motor output systems. For example, sexually dimorphic sensory input from the moth's male-specific antennal sensory neurons, which detect the air-borne female pheromone, has been shown to form specialized connections only with male-specific interneurons in the antennal lobe (Matsumoto and Hildebrand, 1981). Effector organs, such as genital muscles or internal reproductive organs, are often sex-limited, leading to the establishment of segment specific cohorts of motorneurons, as found for example in the abdominal ganglia of moths (Giebultowicz and Truman, 1984; Thorn and Truman, 1989).

In Drosophila certain elements of this species' central and peripheral nervous system, as well as some genital and abdominal muscles, are known to be different in developing or adult males vs. females (Technau, 1984; Lawrence and Johnston, 1986; Stocker and Gendre, 1988; Taylor 1989a,b; Possidente and Murphey, 1989; Taylor and Truman, 1992, Taylor, 1993). However, information regarding the neuronal basis for adult sexually dimorphic behaviors has lagged behind the descriptions of such behaviors and their modification by experience or various mutant genotypes.

Somatic sexual differentiation in the fruit fly *Drosophila melanogaster* is controlled by a genetic regulatory hierarchy that involves the interactions of a number of genes including Sex-lethal (Sxl) transformer (tra), transformer-2 (tra-2) and doublesex (dsx). Each of these genes has been cloned and characterized at the molecular level. Results of these analyses have revealed that the genes function in a cascade of alternative message RNA (mRNA) processing decisions. An effect of this cascade is the production of sex-specific dsx proteins that function as transcriptional regulators that control expression of genes involved in sexual differentiation.

Experiments performed in support of the present invention and described below suggest that fru is a member of the Drosophila sex-determination regulatory hierarchy and is the first gene unique to a previously unrecognized branch of this hierarchy that governs many aspects of male sexual behavior. These experiments have resulted in the elucidation of the nucleotide sequence of portions of the fru locus in Drosophila and cDNA transcripts derived therefrom. According to the teachings presented below, this locus may be an important point in the regulatory hierarchy controlling sexual differentiation in Drosophila. Homologous genes in other organisms may play corresponding roles in the sexual differentiation of those organisms.

As is described more fully below, methods and compositions of the present invention may be used in a variety of ways by one of skill in the art having the benefit of the present disclosure. For example, methods of the present invention may be used to alter the sexual or reproductive behavior of an organism, and/or to identify compounds effective to alter such behavior. One application of such an alteration in sexual or reproductive behavior is pest control, e.g., insect control.

II. Role of fru in Drosophila Sexual Differentiation

Figure 1:
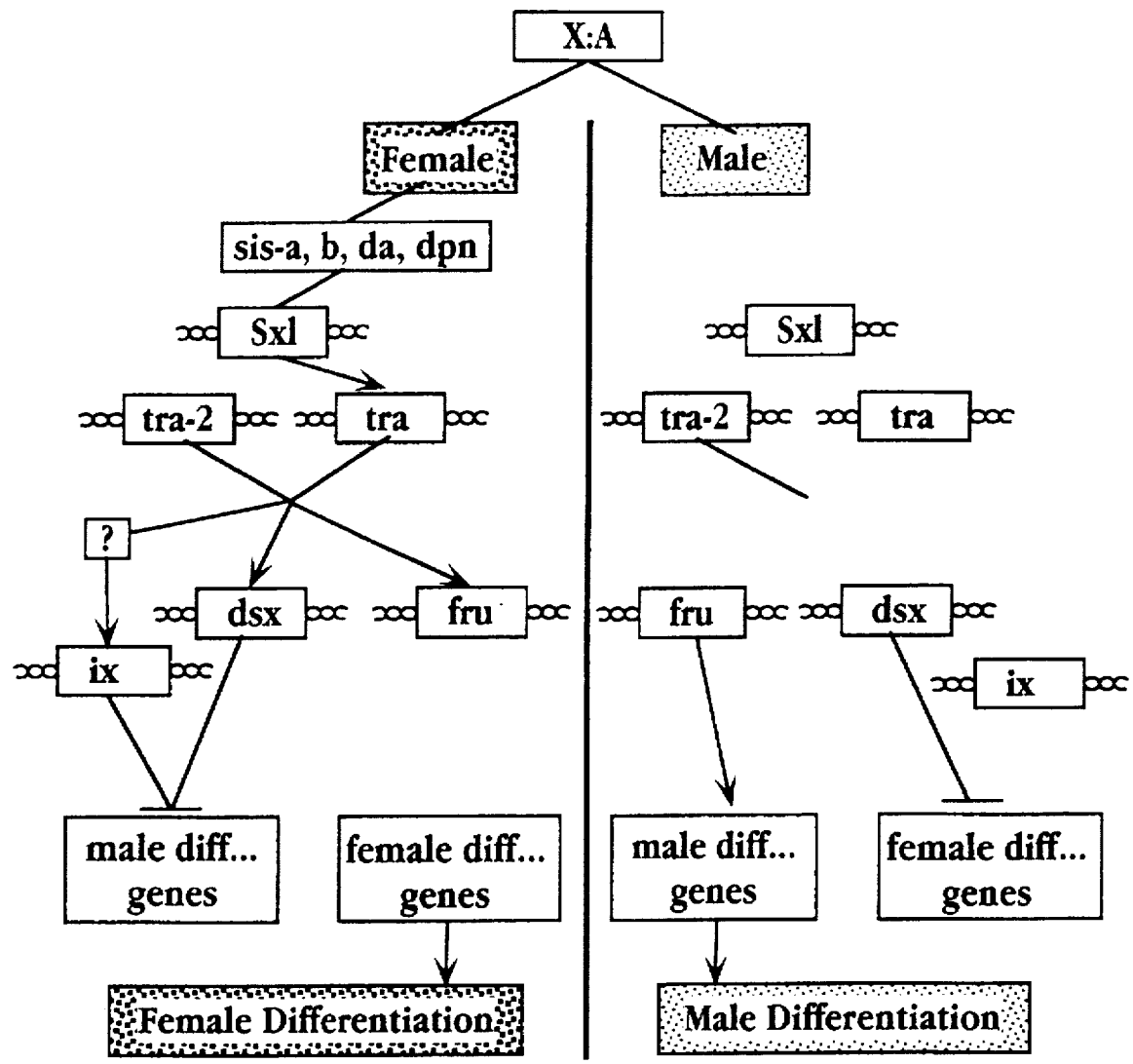
FIG. 1 presents a schematic of a possible sexual differentiation hierarchy in Drosophila.

In *D. melanogaster*, all aspects of sexual differentiation are controlled by a single regulatory hierarchy (reviewed by, for example, Wolfner, 1988; Baker, 1989; Cline, 1988; Hodgkin; 1990; Slee and Bownes, 1990; McKeown and Madigan, 1992). The reference of Harry, et al., (1992), discusses these studies against a background of sex-determination genetics in vertebrates. The hierarchy is comprised of an initial series of steps that are concerned with the determination and establishment of sex. After this point, according to the teachings presented herein, the hierarchy splits into two branches, as is illustrated in FIG. 1. The dsx branch is established in the literature, while the fru branch is based on the results of experiments performed in support of the present invention. The diagram is provided herein as a reference for discussions relating to the possible interactions of other genes and gene products with the methods and compositions of the present invention. The diagram does not necessarily constitute a mechanistic basis for the functioning of the present invention.

A line in the diagram extending from a gene indicates that it is expressed and has an effect on a downstream gene. If the line ends in an arrow the effect is positive; if it ends in a bar the effect is negative. The activity of genes necessary for female development is on the left and for males is on the right. Results of experiments performed in support of the present invention suggest that the action of tra and tra-2 may be to cause the fru pre-mRNA to be spliced into a nonfunctional product in females. In the absence of these activities in males, the fru pre-mRNA may be spliced into a functional product that is important for the expression of male-specific structures and behaviors.

The initial series of steps in the sex determination hierarchy act to assess the X chromosome to Autosome ratio (X:A ratio), which is the primary determinant of sex (Bridges, 1921), and to set the activity of Sex-lethal (Sxl), a master regulatory gene at the top of the hierarchy, to "on" in females and "off" in males (reviewed by, for example, Wolfner, 1988; Baker, 1989; Cline, 1988 Hodgkin; 1990; Slee and Bownes, 1990; McKeown and Madigan, 1992). Once expression of Sxl is initiated in females it is maintained "on" by a positive autoregulatory feedback loop in which SXL protein directs the processing of its own pre-mRNA so as to generate a mRNA that encodes SXL protein (e.g., the reviews cited above). In males, Sxl pre-mRNA is spliced in the default mode which results in the inclusion of a male-specific exon containing stop codons, and hence the male-specific mRNA has no open reading frame.

In addition to regulating the processing of its own pre-mRNA the SXL protein also functions in females to control the activity of two subservient branches to the sexual differentiation hierarchy. One of these branches governs somatic sexual differentiation (see above reviews) and the other dosage compensation (review: Lucchesi and Manning, 1987). To regulate somatic sexual differentiation SXL directs the processing of the pre-mRNA of the transformer (tra) gene in females so as to generate an mRNA with an open reading frame that encodes the TRA protein (Boggs, et al., 1987; Nagoshi et al., 1988). In males, where SXL protein is absent, the trapre-mRNA is spliced by a default pathway, which results in the inclusion of exonic sequences that contain stop codons and hence prevent the synthesis of TRA protein.

In females, the TRA protein (which is female-specific), together with the TRA-2 protein (which is made in both sexes), function to regulate the splicing of the pre-mRNA of the dsx gene to generate a female-specific dsx mRNA (Burtis and Baker, 1989: Nagoshi, et al., 1988; Hedley and Maniatis, 1991; Hoshijima, et al., 1991; Ryner and Baker, 1991). In males, where tra protein is absent, the housekeeping splicing machinery carries out the default pattern of dsx pre-mRNA processing to generate the male-specific dsx pre-mRNA. Both the male- and female-specific dsx mRNAs encode Zn-finger transcription factors, which have identical DNA binding domains, but different carboxy termini. The dsx gene appears to be the last sex-determination regulatory gene in this branch of the hierarchy, since its proteins have been shown to directly interact with the enhancer sequences of at least one of the genes encoding a terminal sexual differentiation function (Burtis, et al., 1991).

One aspect of sexual differentiation, the formation of the Muscle of Lawrence (MOL), does not appear to be controlled by dsx, but is regulated by tra and tra-2 (Taylor, 1992). Results of experiments performed in support of the present invention suggest that the gene immediately below tra and tra-2 in this branch of the hierarchy may be the fruitless gene. In particular, the results suggest that the fru gene may be negatively controlled by tra and tra-2 in females (i.e., the TRA and TRA-2 proteins direct the processing of fru pre-mRNA into an mRNA that does not encode a functional product in females); whereas the default pattern of fru pre-mRNA processing (which occurs in males) may produce an mRNA encoding functional fru product.

Based on the phenotypes of extant fru alleles, the fru branch of the somatic sex determination hierarchy is responsible for the differentiation of the MOL and for expression of normal male courtship behavior. Since both of these phenotypes are determined by the genotype of the nervous system (cf. Siegel et al., 1984, Lawrence and Johnston, 1986), the function of the fru branch may be to control at least some aspects of the differentiation of the CNS, including those responsible for male sexual behavior, and may control other aspects of sexual differentiation. The proposed fru branch may also be required to maintain aspects of sexual differentiation in adult organisms, since normal sexual behavior requires continuous wild type tra-2 function in the adult (Belote and Baker, 1987).

Mutations in the fruitless locus have striking effects on male courtship behavior: fru mutant males initiate courtship of males and females indiscriminately, and are sterile because they are unable to carry out later steps in courtship. Mutations in the fruitless gene affect only males, where their most salient phenotype is that they cause males to initiate courtship with both males and females with equal likelihood.

III. FRU Polynucleotides

A. Molecular Cloning of the Drosophila fru Locus

DNA sequences corresponding to the fru locus in Drosophila were isolated in the course of experiments conducted in support of the present invention. A hybridization probe was designed to isolate fru sequences based on the discovery, disclosed herein, that the dsx and fru genes are regulated by a common factor. The probe, which contains three copies of a 13 nucleotide (nt) regulatory sequence repeated six times in the dsx transcript, was used to screen a Drosophila genomic library as detailed in Example 1. The design and synthesis of the probe are described below in Example 1A—"Generation of Hybridization Probe".

Selective hybridization conditions for the probe were determined (Example 1B—"Selective Hybridization Conditions"), and the probe was used to screen a Drosophila genomic library (Example 1C —"Genomic DNA Library Screen"). Four clones that were good candidates for DNAs containing multiple copies of the 13 nucleotide dsx repeat were isolated (Example 1D—"Southern Blot Analysis of Positive Clones"). The hybridizing fragment from one of these was subcloned into a "BLUESCRIPT SK" phagemid (Stratagene, La Jolla, Calif.) and the clone (pSK(+)11-R) was sequenced. The sequence is presented herein as SEQ ID NO:9, and reveals that the insert contained three copies of the 13 nucleotide repeat.

The clone was further characterized as described in Example 2, and was found to: (i) produce sex-specific transcripts, (ii) reside at cytological location 91B, and (iii) fall within a genomic walk that spans over 100 kbp of the fruitless (fru) gene.

B. Isolation of fru cDNAs

Example 3, below, details an application of the polymerase chain reaction (PCR; Mullis, Mullis, et al.) to obtain the 3'ends of fru cDNA transcripts from male and female mRNA (Example 3A—"RACE PCR"). The isolated RACE products were used to design additional PCR primers, which were employed in nested PCR reactions of CDNA to assay for the presence of fru transcripts. The primers used to detect these transcript were used in a preliminary screen to identify a Drosophila cDNA library containing fru transcripts (Example 3B—"Sex-Specific PCR"). A cDNA library thus identified (a λZAP adult heads cDNA library) was then screened for cDNA clones (Example 3C—"cDNA Library Screen"). Nineteen different fru cDNAs falling into at least 5 different classes (differing through alternative RNA processing) were isolated from this library, and were characterized to determine how they related to each other and to genomic DNA from the region. The results of this characterization are schematized in FIGS. 7D, 7E, 7F, 7G and 7H. The consensus sequence for one of the transcripts (Fru#1) was determined (SEQ ID NO:9), and is shown in FIGS. 9A, 9B and 9C.

C. Isolation of Homologous Sequences from Other Organisms

FRU polynucleotide sequences of the present invention may be used to isolate homologous sequences from other species, including other insects and mammals. In particular, the FRU polynucleotide sequences may be used to isolate corresponding sequences from insects belonging to the phylum Arthropoda (Arthropods), and more particularly, the order Diptera (flies). Examples of Arthropods from which corresponding sequences may be isolated include fruit flies, such as medflies and mexican, mediterranean, oriental, and olive fruit flies (for example, other Drosophila species (sp.), Rhagoletis sp., Ceratitis sp. (e.g., *Ceratitis capitata*) and Dasus sp. (e.g., *Dasus oleae*)), tse-tse flies, such as Glossina sp. (e.g., *Glossina palpalis*), sand flies, such as Phlebo sp. (e.g., *Phlebo tomus*)), blowflies, flesh flies, face flies, houseflies, screw worm-flies, stable flies, mosquitos, northern cattle grub and the like.

Several strategies may be pursued to this end. For example, Southern blots containing DNAs from target species may be probed with a portion of the fru sequence disclosed herein using a series of hybridization conditions to identify those conditions resulting in selective hybridization. An example of how selective hybridization conditions may be experimentally determined is provided in Example 1B. The screen may be conducted with a series of probes (e.g., ~8 probes, each about 250 bp in length) that span the known Drosophila fru sequences.

Effective probes preferably correspond to sequences that are conserved between different species (i.e., coding sequences), and that are not homologous to a large number of non-FRU polypeptides, such as other transcription factors. To this end, portions of the fru coding sequence may be used to search DNA databases, and those regions resulting in a minimal number of homologous "hits" to undesired sequences, such as other transcription factors, may be used as cross-species probes. For example, the sequence between positions 1870 and 2080 of the Fru#1 cDNA (SEQ ID NO:9) is not highly homologous to other sequences present in the DNA databases. Probes derived from this region may be effective at isolating fru homologs from other species.

Alternatively, Northern blots may be screened with a cDNA probe as described above to identify species which may contain fru homolog transcripts. Conditions for selective hybridization may be determined experimentally (e.g., as described in Example 2).

Once selective hybridization conditions are determined, genomic DNA and/or cDNA libraries from the target species are screened to isolate fru homolog DNA fragments. The fragments may be sequenced and the sequences arranged into a consensus sequence spanning the fru homolog region. Alternatively, the sequences may be used as probes for additional screening, extended using RACE PCR approaches (e.g., as in Example 1), and/or used, in combination with sequences disclosed herein, to design degenerate PCR primers for finding fru cognates in yet more distantly related species.

Sequences identified in other species can likewise be used as probes, for example, against genomic and CDNA libraries from that species, to identify the entire genetic locus in that species.

D. Use of FRU Polynucleotides

Polynucleotides of the present invention may be used in a screen for compounds effective to alter the sexual or reproductive behavior of an animal, such as a pest insect. Such a screen may include a reporter gene construct in an expression vector. An expression vector bearing a selectable marker can be constructed with a reporter gene (such as chloramphenicol acetyl-transferase acetyl transferase (CAT), β-galactosidase or luciferase) under the control of, for example, a fru promoter element, and transfected into a selected host cell (for example, Schneider's Line 2 cells or Drosophila Kc cells (Schneider, Ryner and Baker, Hoshijima, K., et al.)). After transfection, effects of test compounds on transcription may be measured by the activity of the reporter gene (e.g. CAT) in, for example, crude cell extracts.

Using FRU probes, non-coding regulatory regions adjacent the FRU coding sequences can be derived from genomic DNA samples, for example, from the λCharon 4A Drosophila genomic library. Using FRU specific primers, both the three and five prime ends of the gene are isolated using the PCR rapid amplification of CDNA ends (PCR-RACE) reaction (Frohman, 1988, 1990). Such 5'non-coding regulatory regions contiguous to 5'FRU coding sequences can be fused to reporter genes such that the reporter gene is in-frame with respect to the location of FRU coding sequences. These reporter constructs can then be transformed into a selected host cell.

Reporter gene systems are well known in the art (see, for example, Ausubel, et al.). Cell lines and vectors used in reporter gene assays are commercially available (for example, Stratagene, La Jolla, Calif.; Clontech Laboratories, Palo Alto, Calif.; Promega Corporation, Madison, Wis.; American Type Culture Collection, 12301 Parklawn Dr., Rockville Md. 20852). One example of a family of commercially-available reporter plasmids are the "pCAT" plasmid (Promega Corp., Madison, Wis.), that contain a CAT transcription unit and an ampicillin resistance gene.

Candidate compounds can be obtained from a number of sources, including but not limited to, the following. Many pharmaceutical and agrichemical companies have extensive libraries of chemical and/or biological mixtures, often fungal, bacterial, or algal extracts, that would be desirable to screen with the assay of the present invention. Such compounds, or molecules, may be either biological or synthetic organic compounds, or even inorganic compounds.

Transfected cells are treated with a selected compound, and the levels of reporter gene product present in treated and untreated cells is determined and compared. Compounds that result in decreased expression of the reporter gene in treated cells are identified as potentially useful sexual behavior-altering compounds. Alternatively, in the case of reporter systems that do not kill or substantially alter the cells, the level of reporter expression may be assayed in the same batch of cells both before (basal level) and after treatment. Levels of expression are compared, and a compound is identified as effective if it significantly depresses the level of expression (relative to the basal level) following treatment.

It will be appreciated that compounds identified as effective in the cells from one species of a group (e.g., insects) may also be effective in other species of that group. In particular, compounds identified as effective in a model system using cells from one species may be tested as described below for effects on other, related species.

Compounds identified by the above screen(s) as potentially effective may be further tested for their ability to alter the sexual or reproductive behavior of a selected organism. For example, a compound identified by the above method may be administered to an insect population to determine if the compound is effective at reducing the reproductive rate of the population.

A variety of insects may be targeted by methods of the present invention. For example, insects belonging to the phylum Arthropoda (Arthropods), and more particularly, the order Diptera (flies) are particularly suitable for targeting by the methods of the present invention. Specific examples of Arthropods which may be targeted include fruit flies, such as medflies and mexican, mediterranean, oriental, and olive fruit flies (for example, Drosophila species (sp.), Rhagoletis sp., Ceratitis sp. (e.g., *Ceratitis capitata*) and Dasus sp. (e.g., *Dasus oleae*)), tse-tse flies, such as Glossina sp. (e.g., *Glossina palpalis*), sand flies, such as Phlebo sp. (e.g., *Phlebo tomus*)), blowflies, flesh flies, face flies, houseflies, screw worm-flies, stable flies, mosquitos, northern cattle grubs and the like.

IV. FRU Polypeptides

A. Production of Recombinant Polypeptides

Polynucleotide sequences of the present invention may be cloned into an expression plasmid, such as p-GEX, to produce corresponding polypeptides. The plasmid pGEX (Smith, et al., 1988) and its derivatives express the polypeptide sequences of a cloned insert fused in-frame with glutathione-S-transferase. Recombinant PGEX plasmids can be transformed into appropriate strains of *E. coli* and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods (Ausubel, et al.).

Affinity chromatography may also be employed for isolating β-galactosidase fusion proteins (such as those produced by lambda gtII clones). The fused protein is isolated by passing cell lysis material over a solid support having surface-bound anti-β-galactosidase antibody.

Isolated recombinant polypeptides produced as described above may be purified by standard protein purification procedures. These procedures may include differential precipitation, molecular sieve chromatography, ion-exchange chromatography, isoelectric focusing, gel electrophoresis and affinity chromatography.

In addition to recombinant methods, FRU proteins or polypeptides can be isolated from selected cells by affinity-based methods, such as by using anti-FRU antibodies (described below). Further, FRU peptides may be chemically synthesized using methods known to these skilled in the art.

B. Use of FRU Polypeptides

Polypeptides of the present invention may be used in a number of ways, including the generation of antibodies. The polypeptides may be used in unmodified form, or they may be coupled to appropriate carrier molecules, such as bovine serum albumin (BSA) or Keyhole Lympet Hemocyanin (KLH) (available from, for example, Pierce, Rockford, Ill.).

To prepare antibodies, a host animal, such as a rabbit, is typically immunized with the purified polypeptide or fusion protein (generated using, for example glutathione-S-transferase as described above). The host serum or plasma is collected following an appropriate time interval, and the serum is tested for antibodies specific against the polypeptide.

The gamma globulin fraction or the IgG antibodies of immunized animals can be obtained, for example, by use of saturated ammonium sulfate precipitation or DEAE Sephadex chromatography, affinity chromatography, or other techniques known to those skilled in the art for producing polyclonal antibodies.

Alternatively, purified antigenic polypeptide or fused antigen protein may be used for producing monoclonal antibodies. In this case, the spleen or lymphocytes from an immunized animal are removed and immortalized or used to prepare hybridomas by methods known to those skilled in the art (e.g., Harlow, et al.). Antibodies secreted by the immortalized cells are screened (e.g., using enzyme linked immunesorbent assay (ELISA) or a Western blot) to determine the clones that secrete antibodies of the desired specificity (e.g., Ausubel, et al.).

Antibodies generated as described above may be used in a variety of ways. For example, antibodies generated against FRU polypeptides may be used in salivary glands to identify the chromosomal locations to which the FRU protein binds on the giant polytene chromosomes of these cells. The resolution available with this technique is such that it is typically possible to ascertain within a few tens of kb where the protein is binding. This enables a relatively rapid identification of the gene in question by determining which genes in the region are expressed in a spatial and temporal pattern consistent with present knowledge of fru expression and male courtship behavior. This approach may also be used in screens of other insects with polytene chromosomes to identify FRU polypeptide targets in those species.

Alternatively, DNA sequences to which the FRU polypeptide binds may be identified, for example, by employing anti-FRU antibodies in DNA/protein interaction assays. Restriction enzyme-digested DNA may be combined with purified FRU protein (and optionally, nuclear extracts from the cells of interest) and size fractionated in duplicate (one preparatory, one analytical) lanes on a polyacrylamide gel. Material from the analytical lane may be blotted and probed with an anti-FRU antibody to determine the location of a FRU-DNA complex in the gel. The complex may then be excised from the corresponding preparatory lane of the gel, and the DNA contained therein may be isolated and cloned for further analysis.

DNA sequences to which the FRU polypeptide binds may be used to identify targets for pest control screens. For example, the approach may be used to identify gene products involved in sexual recognition (distinguishing males from females). This process is thought to involve the reception of pheromone cues by receptors. Genes for such receptors may be targets of regulation by FRU gene products. Identification of pheromone receptors in insects may be used to screen for compounds which affect the functioning of those receptors. Such compounds may find wide application in the area of insect control.

Alternatively, recombinant FRU polypeptides may be labeled (e.g., with $^{125}$I) and used in a screen such as is outlined above to identify DNA fragment that bind the polypeptides. The location of the labeled protein in the blot is determined directly, without the use of an anti-FRU antibody, and corresponding DNA sequences are similarly isolated. DNA sequences identified by any of the methods described above may be used to screen for compounds that interfere with the binding of FRU protein to its target DNA, using screens similar to that described above for the screening of compounds that interfere with the transcriptional activation of fru.

Antibodies generated as described above may also be used to co-immunoprecipitate proteins which interact with FRU polypeptides (partners of FRU). Partners of FRU may be involved in sex-specific or non-sex-specific functions, but the identification of such partners may result in the isolation of new genes involved in sex behavior and/or viability of flies and other insects.

Partners of FRU may also be isolated using, for example, the yeast two-hybrid system. The presence of a BTB domain in FRU polypeptides suggests that the polypeptides are involved in protein-protein interactions. The two hybrid system may be used to isolate polypeptides that interact with FRU polypeptides.

Two hybrid protein interaction assay methods (two hybrid protein-protein interaction screens) provide a simple and sensitive means to detect the interaction between two proteins in living cells. The assays are based on the finding that most eukaryotic transcription activators are modular (e.g, Brent, et al.), i.e., that the activators typically contain activation domains that activate transcription, and DNA binding domains that localize the activator to the appropriate region of a DNA molecule.

In a two hybrid system, a first fusion protein contains one of a pair of interacting proteins fused to a DNA binding domain, and a second fusion protein contains the other of a pair of interacting proteins fused to a transcription activation domain. The two fusion proteins are independently expressed in the same cell, and interaction between the "interacting protein" portions of the fusions reconstitute the function of the transcription activation factor, which is detected by activation of transcription of a reporter gene.

At least two different cell-based two hybrid protein-protein interaction assay systems have been used to assess binding interactions and/or to identify interacting proteins. Both employ a pair of fusion hybrid proteins, where one of the pair contains a first of two "interacting" proteins fused to a transcription activation domain of a transcription activating factor, and the other of the pair contains a second of two "interacting" proteins fused to a DNA binding domain of a transcription activating factor.

The yeast GAL4 two hybrid system (Fields, et al.; Chien, et al.; Durfee, et al.; Bartel, et al.) was developed to detect protein-protein interaction based on the reconstitution of function of GAL4, a transcriptional activator from yeast, by activation of a GAL1-lacZ reporter gene. Like several other transcription activating factors, the GAL4 protein contains two distinct domains, a DNA binding domain and a transcription activation domain. Each domain can be independently expressed as a portion of a fusion protein composed of the domain, and a second, "bait" interacting protein. The two fusion proteins are then independently expressed together in a cell. When the two GAL4 domains are brought together by a binding interaction between the two "interacting" proteins, transcription of a reporter gene under the transcriptional control of GAL4 is initiated. The reporter gene typically has a promoter containing GAL4 protein binding sites (GAL upstream activating sequences, $UAS_G$).

In one example of the use of a two hybrid system to isolate partner(s) of FRU, a FRU polypeptide is fused to the GAL4 DNA binding domain (G4BD) in a yeast expression vector (pG4AD-FRU). The vector is used to generate yeast cells harboring pG4AD-FRU and a GAL4-activated reporter gene (e.g., LacZ), which are then transformed with one of three fusion libraries. Each library carries fusions between the transcription activating domain of yeast GAL4 (G4AD) and insect (e.g., Drosophila) genomic DNA restriction enzyme fragments (e.g., Sau3A1 fragments) in one of the three reading frames.

The yeast cells containing the libraries are screened (e.g., using a β-galactosidase (β-gal) assay on plates containing the chromogenic substrate X-gal) for expression of the reporter. Reporter-expressing cells are identified as possibly containing Sau3A1 DNA fragments encoding polypeptides capable of interacting with the FRU polypeptide.

A second two hybrid system, described in detail in Ausubel, et al., utilizes a native *E. coli* LexA repressor protein, which binds tightly to appropriate operators. A plasmid is used to express one of a pair of interacting proteins (the "bait" protein) as a fusion to LexA.

The plasmid expressing the LexA-fused bait protein is used to transform a reporter strain of yeast, such as EGY48. In this strain, binding sites for LexA are located upstream of two reporter genes. In the first reporter system, the upstream activation sequences of the chromosomal LEU2 gene—required in the biosynthetic pathway for leucine (Leu)—are replaced in EGY48 with lexA operators, permitting selection for viability when cells are plated on medium lacking Leu. In the second reporter system, EGY48 harbors a plasmid, pSH18-34, that contains a lexA operator-lacZ fusion gene, permitting discrimination based on color when the yeast is grown on medium containing Xgal (Ausubel, et al.).

LexA and GAL4 each have different properties that should be considered when selecting a system. LexA is derived from a heterologous organism, has no known effect on the growth of yeast, possesses no residual transcriptional activity, can be used in GAL4+yeast, and can be used with a Gal-inducible promoter. Because GAL4 is an important yeast transcriptional activator, experiments must be performed in gal4[31] yeast strains to avoid background from endogenous GAL4 activating the reporter system. Both two hybrid systems have been successfully used for isolating genes encoding proteins that bind a target protein and as simple protein binding assays (e.g., Yang, et al., Gyuris, et al.), and both can be applied to the identification of polypeptides that interact with the FRU polypeptide.

V. Generation of New Fru Phenotypes Modified fru constructs may be reintroduced into flies to generate Fru alleles with dominant behavioral and/or sterility phenotypes. Such constructs include those in which either the DNA binding domain or the N-terminal BTB domain are truncated, as well as constructs that ectopically express fru cDNAs under a ubiquitous (e.g., hsp70) promoter.

While the presently-known alleles of fru are recessive, many loci in Drosophila have both dominant and recessive alleles. One such locus, doublesex (Baker and Ridge, 1980), is also involved in the regulatory hierarchy controlling sexual differentiation and is a Zn finger-containing transcription factor (Burtis and Baker, 1989).

Constructs effective at conferring dominant sterile phenotypes may be engineered into vectors suitable for transforming other types of insects, such as insects belonging to the phylum Arthropoda (Arthropods), and more particularly, the order Diptera (flies). Specific examples of Arthropods which may be transformed include flies, such as medflies and mexican, Mediterranean, oriental, and olive fruit flies (for example, Drosophila species (sp.), Rhagoletis sp., Ceratitis sp. (e.g., *Ceratitis capitata*) and Dasus sp. (e.g., *Dasus oleae*)), tse-tse flies, such as Glossina sp. (e.g., *Glosisna palpalis*), sand flies, such as Phlebo sp. (e.g., *Phlebo tomus*)), blowflies, flesh flies, face flies, houseflies, screw worm-flies, stable flies, mosquitos, northern cattle grub and other pests.

Such transgenic insects have been made by injecting a vector containing cloned DNA and a selectable marker into embryos and selecting transgenic progeny (Miller, et al.). Mutant insects produced in this manner may be grown and used in sterile-release programs to aid in controlling pest insect populations. Such programs have been demonstrated to be successful in controlling insect pest populations (see, for example, Wong, et al., Calkins, et al.).

Specimens made sterile by the introduction of a dominant mutation of Fru or its homologs offer an advantage in that the sterility gene is propagated through a series of generations by females carrying the mutation mating with wild-type males. Of course, the sterile males also aid in reducing the population by (fruitlessly) courting both wild-type males and females.

The following examples illustrate but in no way are intended to limit the present invention.

MATERIALS AND METHODS

Unless indicated otherwise, chemicals and reagents were obtained from Sigma Chemical Company (St. Louis, Mo.) or Mallinckrodt Specialty Chemicals (Chesterfield, Mo.), restriction endonucleases were obtained from New England BioLabs (Beverly, Mass.), and other modifying enzymes and biochemicals were obtained from Pharmacia Biotech (Piscataway, N.J.), Boehringer Mannheim (Indianapolis, Ind.) or Promega Corporation (Madison, Wis.). Materials for media for cell culture were obtained from Gibco/BRL (Gaithersburg, Md.) or DIFCO (Detroit, Mich.). Unless otherwise indicated, manipulations of Drosophila, cells, bacteria and nucleic acids were performed using standard methods and protocols (e.g., Ashburner; Sambrook, et al.; Ausubel, et al.).

EXAMPLE 1

Molecular Cloning of the fru Gene Locus

A. Generation of Hybridization Probe

A DNA probe (SEQ ID NO:1) containing 3 copies of the dsx 13 nucleotide (nt) repeated sequence was generated as follows. Two 21 nucleotide complementary single-stranded (ss) oligonucleotides (SEQ ID NO:2, SEQ ID NO:3) were synthesized by the Pan Facility (Beckman Center B065, Stanford University Medical Center, Stanford, Calif.).

The oligonucleotides were hybridized to each other by heating a solution containing equimolar amounts of the two oligonucleotides (130 µg of each) to 95° C. in a heater block, and then removing the block from the heater and allowing it to cool to room temperature over approximately 30 minutes.

The resulting double-stranded (ds) DNA fragment contained complementary four base 5' protruding ends. The 5'ends were phosphorylated with 2 mM ATP and 20 units of polynucleotide kinase (New England BioLabs, Beverly, Mass.) for 2 hours at 37° C. The DNA was then ethanol precipitated and resuspended in 40 µl of water.

The phosphorylated dsDNA fragment was multimerized using T4 DNA ligase (New England BioLabs) by incubating the whole DNA sample (260 µg) in ligation buffer (New England BioLabs) containing 30 units of T4 DNA ligase for 1 hour at 20° C. The reaction mixture was then digested with 100 units of restriction endonucleases BamHI and BglII (New England BioLabs) for 1 hour under conditions recommended by the manufacturer. This procedure digested molecules ligated together in opposite orientations. Multimers comprised of repeat fragments having the same orientation remained intact. The reaction mixture was then cooled on ice, mixed with gel loading buffer, and the DNA fragment multimers contained therein were size fractionated by agarose gel electrophoresis on a 1.5% gel.

Multimers ranging from about 63 bases to about 126 bases in length were excised from the gel, partially purified by electroelution (Sambrook, et al.), and subcloned into the unique BamHI restriction endonuclease site of the phagemid "BLUESCRIPT SK(+)" (Stratagene, La Jolla, Calif.). The inserts of several clones were sequenced, and an isolate (pSK(+)3XR) containing 3 copies (3× repeats) of the synthetic dsDNA fragment was identified. This plasmid was further modified by deleting the region between the KpnI and PstI restriction sites to facilitate a higher level of incorporation of radioactive nucleotides into hybridization probes made from the plasmid.

A single stranded (ss) radioactive probe was generated as follows: ssDNA was obtained from the f1 ori-containing pBSK(+)3×R upon co-infection of the host cells with helper phage following manufacturer's instructions (Stratagene). One µg of the ssDNA was combined with 2.5 ng of −20 primer (SEQ ID NO:4), 5 units of Klenow fragment (GIBCO BRL Research Products/Life Technologies, Gaithersburg, Md.), 70 µCi each of $\alpha$-$^{32}$P-dCTP and a-$^{32}$P-dATP, and 30 µM each dGTP and dTTP cold nucleotides in 30 µl of 20 mM Tris-HCl, pH 8.5, 10 mM $MgCl_2$ buffer to make a labeled complementary copy of the single stranded template (Burtis and Baker, 1989).

The radioactively-labeled insert portion of the plasmid was excised by digestion with XbaI and BamHI and was gel purified using low melting-point agarose ("NUSIEVE GTG"; FMC BioProducts, Rockland, Me.). The gel slice containing the probe was melted and added directly to hybridization reactions described below.

B. Selective Hybridization Conditions

Selective hybridization conditions for library screening were determined as follows. 4 μg of total genomic Drosophila DNA was digested with EcoRI or BamHI, size fractionated by 0.9% agarose gel electrophoresis and transferred to a nylon membrane (Schleicher & Schuell, Keene, N.H.).

Figures 2A, 2B:
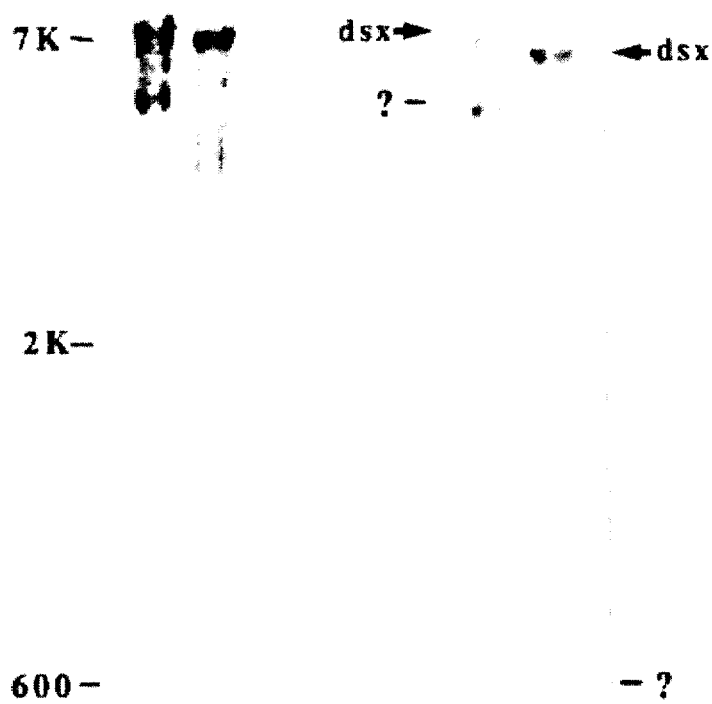
FIGS. 2A and 2B show images of a Southern (Drosophila DNA) blot probed with a 3× dsx repeats probe. The blot in FIG. 2A was washed at 47° C., while the blot in FIG. 2B was washed at 51° C.

The membrane was hybridized overnight with the 3× repeats probe under standard conditions (Sambrook, et al.), using 6× SSC, 5× Denhardt's reagent, 0.5% Sodium dodecyl sulfate (SDS), and 100 μg/ml denatured and sheered salmon sperm DNA (no formamide) at 42°C. Following hybridization, the filter was washed under the same salt conditions but at increasing temperatures. The results are shown in FIGS. 2A (47° C. final wash) and 2B (51° C. final wash). The 47° C. wash resulted in detection of several bands in both the BamHI and EcoRI digests. Only two prominent fragments were observed in both digests following the 51° C. wash. In both digests, one of the fragments is of the size expected for the dsx-containing fragment (indicated with arrows), and the other, having a smaller size (~600 bp in the EcoRI digest and ~5 kb in the BamHI digest), is indicated by a "?".

These results suggest that the hybridization probe is detecting sequences from two genes—the dsx gene from which it was designed, and a second, unidentified gene.

C. Genomic DNA Library Screen

The labeled 3× repeats probe described above was used to screen a lambda Charon 4A (Maniatis, et al., 1978) Drosophila genomic library for homologous sequences. As equivalent of eight genomes' worth of DNA were screened using the conditions described above with a 40° C. final wash.

Forty two positive plaques were detected. Eight of these were determined to be from dsx. The remaining 34 were isolated and compared with each other using cross-hybridization analysis, which indicated that the 34 non-dsx clones represented 12 different sets of clones.

D. Southern Blot Analysis of Positive Clones

Figure 3A:
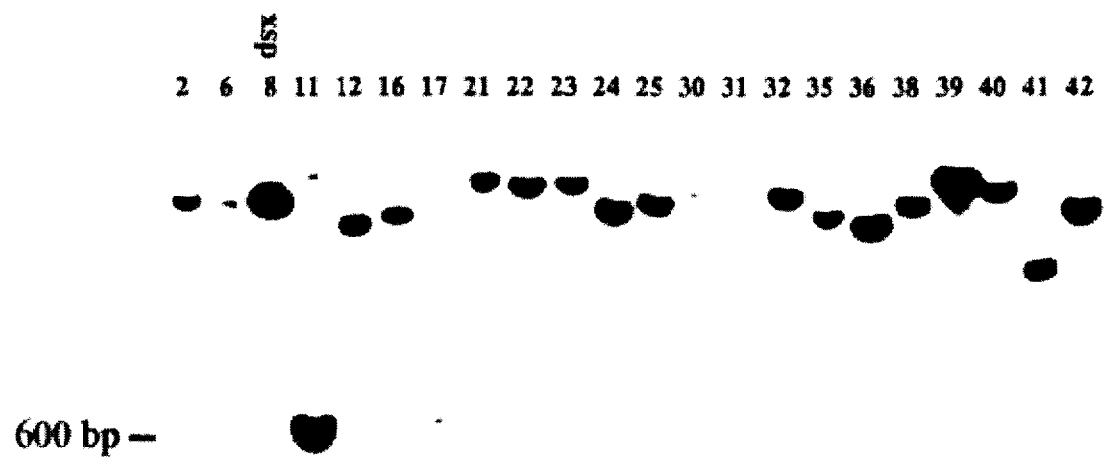
FIGS. 3A and 3B show images of a Southern blot containing DNA from a set of Drosophila genomic clones probed with a 3× dsx repeats probe (FIG. 3A) or with a second probe containing 5 dsx repeats (FIG. 3B).

The clones were further characterized by Southern analysis. One clone from each set was digested with EcoRI, size-fractionated on a gel, and blotted onto a nitrocellulose filter. The filter was hybridized with the 3× repeat probe and washed at 40° C. as above. Hybridizing bands were detected by autoradiography (FIG. 3A). The same filter was then hybridized again with a second probe containing 5 copies of the 13 nt repeat sequence (but no other sequence in common with the first probe). The second probe was generated from a 260 base-pair (bp) fragment of dsx (positions 2793 to 3053; Burtis and Baker, 1989). The filter was washed and subjected to autoradiography as above, and is imaged in FIG. 3B.

Figure 3B:
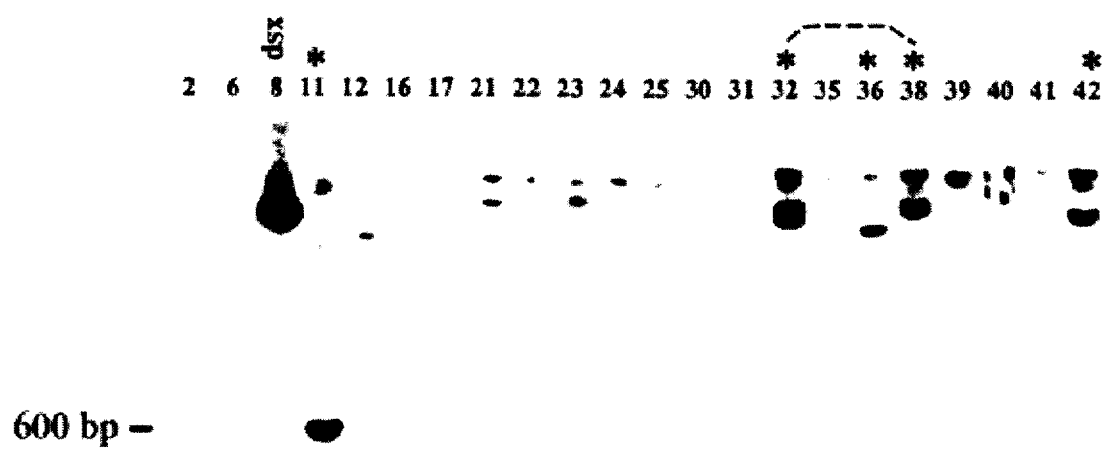

Four of the clones, indicated in FIG. 3B by "*", hybridized with both probes and were thus considered to be the best candidates for non-dsx DNA containing multiple copies of the 13 nt repeat sequence. One of these (FIGS. 3A and 3B, lanes labelled 11), representing eight of the 34 originally-identified non-dsx clones, had a particularly strong hybridization signal. This lambda phage clone, termed λCh4A-11, was characterized further as described below.

E. Sequence Analysis of a Candidate Clone

Clone λCh4A-11 contained a ~600 bp EcoRI insert which hybridized to the 3× repeat probe. This fragment was isolated and subcloned into the EcoRI site of pBluescript SK(+), generating pSK(+)11-R. Approximately 550 bp of the ~600 bp insert of pSK(+)11-R were sequenced using standard dideoxy termination sequencing reactions (Sanger, et al.) with a "SEQUENASE 2.0" sequencing kit (United States Biochemical, Cleveland, Ohio). The sequence (presented in FIG. 4 and as SEQ ID NO:11) revealed that the clone contained 3 copies of the 13 nt dsx repeat sequence (indicated by boxes in FIG. 4). Also indicated in FIG. 4 is the location of the two EcoRI sites. Bases whose sequence was not precisely determined are indicated by "N". The seven remaining clones in the set represented by λCh4A-11 also contained the ~600 bp EcoRI fragment (SEQ ID NO:11) that hybridized strongly to the 3× repeats probe.

EXAMPLE 2

Characterization of pSK(+)11-R

A. Northern Blot Analysis

Figures 5A, 5B:
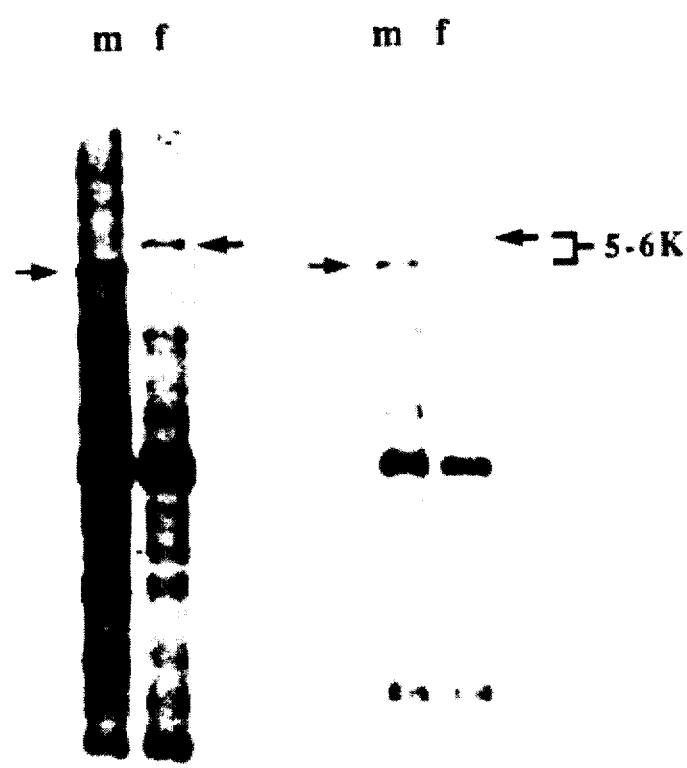
FIGS. 5A and 5B present images of Northern (sex-specific Drosophila poly(A)+RNA) blots probed with the ~600 kb EcoRI DNA fragment shown in FIG. 4, and washed at 40° C.

To test whether the genomic fragment insert was from a transcription unit, an anti-sense radioactive riboprobe was synthesized from the ~600 bp insert of pSK(+)11-R using standard techniques (Sambrook, et al.) and used to probe a blot containing poly(A+) male and female RNA from whole adult flies (FIG. 5). The sense/antisense orientation of the insert was deduced from a comparison of the 13nt repeat sequence in the clones with the same repeat sequences in dsx. The blot was hybridized at 65° C. using standard RNA blot hybridization techniques (Sambrook, et al.), washed at 40° C., imaged (FIG. 5A), washed at 65° C., and imaged again (FIG. 5B). Imaging was done using autoradiography.

The RNA was isolated using standard methods. Briefly, adult flies were homogenized in 4M guanidium isothiocyanate, 10 mM EDTA, 100 mM Tris pH 7.5 and 1% β-mercaptoethanol, then layered onto a 5.7M CsCl, 0.1 M EDTA cushion and centrifuged at 150,000×g for 12 hours. The RNA pellet was then resuspended in 10 mM Tris-HCl pH 7.5, 5 mM EDTA and 0.1% sodium dodecyl sulfate (SDS). After phenol extraction and ethanol precipitation the RNA was selected on oligo d(T) cellulose type 7 (Pharmacia, Piscataway, N.J.) as described in Sambrook, et al.

The images, shown in FIGS. 5A and 5B, detected the presence of at least 4 transcripts, 2 of which (arrows in FIGS. 5A and 5B) appeared to be expressed in a sex-specific manner (one in each sex). A ~5 kilobase (kbp transcript was expressed in males ("m") and a ~6 kbp transcript was detected in females ("f").

B. Chromosomal Localization

In situ hybridization on squashes of salivary gland polytene chromosomes (Ashburner) was carried out to determine where on the Drosophila chromosomes the set of clones represented by clone pSK(+)11-R resides. DNA from 2 of the 8 overlapping lambda phage clones (clones λCh4A-11 and ~Ch4A-19) was used to generate biotinylated probes (Ashburner), which were used to probe polytene chromosome squashes using standard methods (Ashburner). The probes hybridized to cytological location 91B, suggesting that the sequences isolated herein may correspond to the fru gene, whose locus also resides at 91B. Further evidence linking the clones to the fru locus was obtained from results showing specific hybridization of the clones to DNAs obtained during a genomic walk spanning the fru-containing region of chromosome 3.

EXAMPLE 3

Isolation of fru cDNAs

Three different cDNA libraries from *Drosophila melanogaster*, including Xnvx male larval and female larval cDNA libraries (obtained from Dr. S. Elledge, Baylor College of Medicine, Houston, Tex.) and a λgt10 larval disc cDNA library (obtained from Drs. A. Cowman and G. Rubin, University of California, Berkeley, Calif.), were screened by conventional methods using a probe generated from the insert of clone pSK(+)11-R. However, no fru cDNAs were detected in these screens, presumably due to low levels of fru expression.

A. RACE PCR

Due to the apparent rarity of fru mRNA, a 3' end anchored (Frohman, et al.) polymerase chain reaction (PCR; Mullis, Mullis, et al.) approach was employed to isolate fru transcript(s). Two nested primers (fru-1—SEQ ID NO:5; fru-2—SEQ ID NO:6) were synthesized as above. The sequences of the primers corresponded to sequences near the 5' end of the pSK9(+)11-R insert. The locations corresponding to the primer sequences are indicated by arrows, labeled as "1" (fru-1) and "2" (fru-2), in FIG. 6A, which shows a schematic of the ~600 bp insert of pSK9(+)11-R. The positions of the 13 nt repeat sequences are shown as black boxes in FIG. 6A.

A 3' RACE kit (GIBCO BRL Research Products/LIFE TECHNOLOGIES, Inc., Gaithersburg, Md.) was used to generate PCR products from poly (A+) RNA, isolated as described above, from either adult males or adult females. Specific amplification products (~400 bp from male RNA and ~450 bp from female RNA) were detected and determined to contain sequences having homology to the pSK(+)11-R insert by Southern analysis. The PCR products were subcloned and partially sequenced. The sequences corresponded to the sequence near the 5'end of the pSK(+) 11-R insert, which appeared to be spliced at a site just downstream of the repeats to different downstream exons. The male- and female-specific 3'RACE products are shown schematically in FIGS. 6B and 6C, respectively, in relation to the pSK(+)11-R insert shown in FIG. 6A.

B. Sex-Specific PCR

To confirm that the isolated 3'RACE products reflected the structure of authentic fru transcripts, new primer sets were synthesized from sequence of the putative male and female PCR products. The positions of these primers are indicated in FIGS. 6B and 6C by arrows. The male primer, fru-5-rev, had the sequence represented by SEQ ID NO:7 and the female primer, fru-4-rev, had the sequence represented as SEQ ID NO:8. These sex-specific primers were paired with fru-1 and fru-2 primers to generate nested primer sets for two rounds of the PCR. The first round was performed with fru-1 and either fru-4-rev or fru-5-rev, and the second round with fru-2 and again with either fru-4-rev or fru-5-rev.

These primer sets were used to amplify CDNA generated from several different batches of male- and female-specific poly (A+) RNA. The "female" 3' RACE product, amplified by primers fru-2 (SEQ ID NO:6) and fru-4-rev (SEQ ID NO:8) was subsequently consistently detected in different batches of RNA from both sexes, suggesting that it corresponded to a portion of an authentic fru mRNA. Due to the relatively small size of this fragment (450 bp) as compared to the fru transcripts detected in Northerns (~5–6 kbp; see above), this fragment most likely did not contain a full-length fru transcript. To isolate full-length cDNA transcripts, the same primer set (primer fru-2 (SEQ ID NO:6) and fru-4-rev (SEQ ID NO:8) was used in a preliminary screen of a series of Drosophila cDNA libraries to identify those libraries which contained fru transcripts.

Libraries screened included the three listed above plus a λgt10 adult heads cDNA library (obtained from Dr. A. Cowman) and a λZAP (Stratagene, LaJolla, Calif.) adult heads cDNA library (obtained from Dr. T. Schwarz, Stanford University, Stanford, Calif.; DiAntonio, et al.). The only consistent positive results obtained with the preliminary screen were with the lambda ZAP head cDNA library. Accordingly, this library was screened to isolate fru cDNA clones, as described below.

C. cDNA Library Screen

Two-thirds of the complexity of the lambda ZAP head CDNA library described above were screened using conventional methods with labeled "female" 3'RACE product as a probe.

Nine different overlapping cDNAs were isolated. They were characterized by restriction mapping and Southern analysis, including hybridization to the DNAs from the genomic walk, and by cross hybridization to each other. These cDNAs represented at least 3 different classes of transcripts. However, none had the exact structure of the 3'RACE product that was used as the probe to detect them, suggesting that these cDNAs represented only a subset of fru transcripts.

Accordingly, the library was rescreened with various portions of the 9 cDNAs. This screen resulted in the identification of 10 new cDNAs that overlapped each other as well as the 9 previously identified cDNAs. Molecular analysis of the new cDNAs revealed two additional classes of transcripts, including one that contained the sequence found in the "female" 3' RACE product.

A member of each of the five classes was mapped to the DNAs from the genomic walk described above. Fragments from the 5' parts of the cDNA clones mapped to two regions in the distal half of the walk. The 3' end portions of the cDNAs did not hybridize to the walk. The walk was therefore extended in the proximal direction using the cosmid HX1 (obtained from Dr. K. Moses, University of Southern California, Pasadena, Calif.; Moses, et al.), which overlaps the proximal end of the walk. This cosmid was restriction mapped, digested, and blotted for Southern analysis with probes from the 3' end portions of the cDNAs.

Results from the above analyses are shown schematically in FIGS. 7A, 7B, 7C, 7D, 7E, 7F, 7G and 7H. 5' to 3' is from right to left. FIG. 7A shows a schematic of the DNA fragments isolated (f10A, f9A, f3A, f2A, f1D, f1H, f4B, f5C and f7A) as part of a genomic walk spanning the fru locus, as well as a schematic of the location of the HX1 cosmid, relative to the map of the fru region shown in FIG. 7B. FIG. 7B shows a schematic of the fru region of chromosome 3, indicating the positions of know fru lesions (mutants fru-2, fru-4, fru-3 and fru-1). The numbers on the scale correspond to kilobases. fru-1 is depicted by a zig-zag line to indicate an inversion breakpoint, while fru-2, fru-3 and fru-4 are shown as boxes to indicate insertion of P-element sequences. FIG. 7C shows a schematic of two fru deficiencies, Df(3R)P14 and Df(3R)ChaM5, relative to the map of the fru region shown in FIG. 7B.

FIGS. 7D, 7E, 7F, 7G and 7H show schematic diagrams of the location of sequences comprising five fru cDNA transcripts relative to the map of the fru region shown in FIG. 7B. Exons are indicated as boxes and introns as lines. The dark boxes near the 3' ends of the transcripts correspond to exons that contain potential Zn finger sequences, discussed below. The locations of the 13 nt dsx repeats are indicated by "*".

The results indicate that the 3' ends of the cDNAs correspond to the genomic region spanned by HX1, and demonstrated that fru transcripts can contain alternative 3' end exons.

D. Sequence Analyses of cDNA Clone Fru#1

One of the isolated cDNAs (shown schematically in FIG. 7D) was sequenced in its entirety. The consensus sequence of this transcript (FIG. 9A, 9B, and 9C; SEQ ID NO:9), termed Fru#1, contains one long open reading frame that encodes a 675 amino acid polypeptide (SEQ ID NO:10). The sequence was used to search the Swiss-prot 30 and PIR 42 data bases for homologous sequences (using software from IntelliGenetics Inc., Mt. View, Calif.). Further, SEQ ID NO:10 was scanned for protein motifs using IntelliGenetics "QUEST" software and the "PROSITE 12" data bank. These analyses revealed the presence of a highly conserved N-terminal domain, termed BTB domain, found in a number of known transcriptional factors (Zollman, et al.), and a single zinc (Zn) finger at the C-terminal of the Fru#1 cDNA (suggesting the presence of a DNA binding domain).

A schematic of the Fru#1 polypeptide is shown in FIG. 8. Three copies of the 13 nt repeat sequence are found in the 5' untranslated region just upstream of the ATG initiation codon. The polypeptide contains a BTB domain adjacent the repeats and a Zn finger domain near the C-terminus. The nucleotide sequence of Fru#1 is shown in FIG. 9A, 9B and 9C. The 13 nt repeat regions are underlined, the coding sequence is capitalized, and the ATG initiation codon and TAA termination codon are in bold.

While the invention has been described with reference to specific methods and embodiments, it is appreciated that various modifications and changes may be made without departing from the invention.

---

It is claimed:

1. A method of identifying a compound effective to alter the reproductive behavior of a target insect, comprising treating an insect cell with a test compound, where said cell is obtained from the target insect and carries an expression vector containing FRU regulatory sequences operably linked to a reporter gene, evaluating the level of expression of the reporter gene in the treated cell, and identifying the compound as effective if said compound significantly decreases the expression of the reporter gene in the treated cell relative to the expression of the reporter gene in untreated cells carrying said expression vector.

2. The method of claim 1, wherein the reporter gene encodes a protein selected from the group consisting of chloramphenicol acetyl-transferase (CAT), β-galactosidase (β-gal) and luciferase.

3. The method of claim 1, wherein the target insect is a Drosophila species, and the cells are selected from the group consisting of Schneider's Line 2 and Drosophila Kc cells.

4. The method of claim 1, wherein the regulatory sequences are from Drosophila.

5. The method of claim 1, wherein the target insect is a member of the phylum Arthropoda.

6. The method of claim 5, wherein the target insect is a member of the order Diptera.

7. The method of claim 5, wherein the target insect is selected from the group consisting of medfly, fruit fly, tse-tse fly, sand fly, blowfly, flesh fly, face fly, housefly, screw worm-fly, stable fly, mosquito, and northern cattle grub.

8. An isolated FRU polynucleotide.

9. The polynucleotide of claim 8, wherein the polynucleotide is selected from the group consisting of RNA, cDNA and genomic DNA.

10. The polynucleotide of claim 8, wherein the polynucleotide is derived from an insect that is a member of the phylum Arthropoda.

11. The polynucleotide of claim 10, wherein the polynucleotide is derived from an insect selected from the group consisting of medfly, fruit fly, tse-tse fly, sand fly, blowfly, flesh fly, face fly, housefly, screw worm-fly, stable fly, mosquito, and northern cattle grub.

12. The polynucleotide of claim 10, wherein the polynucleotide is derived from an insect that is a member of the order Diptera.

13. The polynucleotide of claim 12, wherein the polynucleotide is derived from a Drosophila polynucleotide.

14. The polynucleotide of claim 13, wherein the polynucleotide contains the sequence represented as SEQ ID NO:9.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 63 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: 3x repeat probe ( x i ) SEQUENCE DESCRIPTION: SEQ ID NO:1:

```
GATCCATCTT CAATCAACAT AGATCCATCT TCAATCAACA TAGATCCATC TTCAATCAAC        60
ATA                                                                     63
```

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: sense dsx repeat 21-mer ( x i ) SEQUENCE DESCRIPTION: SEQ ID NO:2:

```
GATCCATCTT CAATCAACAT A                                                 21
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (  i i  ) MOLECULE TYPE: DNA (  i i i  ) HYPOTHETICAL: NO (  i v  ) ANTI-SENSE: NO (  v i  ) ORIGINAL SOURCE:
  ( C ) INDIVIDUAL ISOLATE: antisense dsx repeat 21-mer (  x i  ) SEQUENCE DESCRIPTION: SEQ ID NO:3:

GATCTATGTT GATTGAAGAT G     21

( 2 ) INFORMATION FOR SEQ ID NO:4:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: -20 sequencing primer ( x i ) SEQUENCE DESCRIPTION: SEQ ID NO:4:

GTAAAACGAC GGCCAGT     17

( 2 ) INFORMATION FOR SEQ ID NO:5:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: fru-1 primer ( x i ) SEQUENCE DESCRIPTION: SEQ ID NO:5:

GACGTGTGAC GATGGAGCAA C     21

( 2 ) INFORMATION FOR SEQ ID NO:6:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: fru-2 primer ( x i ) SEQUENCE DESCRIPTION: SEQ ID NO:6:

CGATCCAGAT CGAAAGAGAA TATCATC     27

( 2 ) INFORMATION FOR SEQ ID NO:7:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: fru-5 rev primer ( x i ) SEQUENCE DESCRIPTION: SEQ ID NO:7:

```
GCTGTCGACA TGCCATAGGT GAATAGGC                                    28
```

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: fru-4 rev primer ( x i ) SEQUENCE DESCRIPTION: SEQ ID NO:8:

```
AGGCGTGATC ATTATGATAT TGTAGCAA                                    28
```

( 2 ) INFORMATION FOR SEQ ID NO:9:

( i ) SEQUENCE CHARACTERISTICS:
        ( A ) LENGTH: 4835 base pairs
        ( B ) TYPE: nucleic acid
        ( C ) STRANDEDNESS: double
        ( D ) TOPOLOGY: unknown ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: Fru#1 cDNA ( i x ) FEATURE:
        ( A ) NAME/KEY: CDS
        ( B ) LOCATION: 1507..3534

( x i ) SEQUENCE DESCRIPTION: SEQ ID NO:9:

```
GAATTCGGCA CGAGATTCAC CTATGGCATA TCATCAGCAA CACACATCAA CGCACTTCTC    60
TGCTATGTCT GCAATCAACC AAAATATCAA AAAAAAAAG  AAAAACAAAA AGAGTCAACA   120
TCAATTTTAA AGTTTTTACG TTGGTTCGAA AGAGTTTAAA ATGCCCTTAA CTATTAACGC   180
CCAAAAGTAA ACGTAGATTA AGTAATATT  AGCCAATCAA TCGTAAAATA TCAGCTTTCG   240
TTTTTTAAAA CTTACCAATG GACTTTGATC CCATCAATTG CAAATCTAAA GTAGAGAAAT   300
AGAGAGAGAT AAGAGATATA ATATCACTAA CCAAAAGTGT TGCCACGAG  TATTAAAATG   360
TTAACTACTA CAATAGAATA CGTATTCTTG TTTCCTTCGC TAGTATGTAT AAGCAAACTA   420
```

```
ACTGCAAGAA ACAACACCAA CTAATTAATA TTTAATAGCA TAATGGTAAT ATCGTAAGAA      480
TATCATAGAT TTAAGGCAGA GCATTTCAGA CAGCACTTGT ACCGTTCTAG ACTTAAGTAT      540
TCGAAGTATA CGTAACTCAA GCAATCCAAT AACAATAACT AAGTAGAAGT TCTTTTCAAA      600
ATAATACTAT ACACGAATCC TTCAGTCAAA CCCCCTACAA TATTACTTAG ATAAACATAT      660
AGTATTATAT AGCCAAAGCC AGGAAAGGAG TTGTAAGCCA TTGCATATAT ATATTTGGTA      720
GATAAAGAAC AGCTAACGAA AGGGTCCACA AGCTACCCAT AACTTACTTA GAATAACTAA      780
ACACAACTAG CCAAGAAGTA GATATCTATA TATATATCGA GTTTGCTAA CATCAAAGTA       840
TACGTAAATT GAAAACCAAG AATTTTGCCT AGCTTAAATA ACACTCTTTC AAAGCAATAC     900
CATAAACAAT AATTACAAGT TAACGCAACT AAACACATAT TGTATACCAG ATAGTTTATG    960
CCTAAACACT ACTAGTAGCC CTAAGTCCTA GGCATAAACC GAGCACCACG GCGAGATATG    1020
CACCCATGTA AAATGCAGAA ATTAATTACC AAGAGTACAA ACTGTAAAGG AAACCCCTAT    1080
TGAAGCTCAA TTGGCCAGCC CATCTAGTGT AGCGCTAAGT AGTTCGTAAT CGTAAGCAAT    1140
TGTAAGGCAA ACACTTTTCA AGTGAGCGAA ATATCAAGCA AACTGTGAGA ATTCGAGGAC    1200
GTGTGACGAT GGAGCAACCC TTCCCCCCCA GATCGAAAGA GAATATCATC AATCAACATT    1260
CCCGTGCCCG GAGGAGCTGC TCTTCAATCA ACACTCAACC CGAACTGGGC CCTCAAAAGC    1320
CCGGCAACCT AAAGTTAGTC CTTTCATTAG CCTCTTCTAT CAATTAGTTA GTCAGCCAAC    1380
GTTTCTCTCT CTCTCATAAT TCTAACCGAA AGTAAGCATA GAAAAGAACC AATACTTCAA   1440
TCAACATACC CACAAAAAAA AACAAATCCC CACCAACTGG CGCGGTACAA CACTGACCAA    1500
GGAGCG ATG GAC CAG CAA TTC TGC TTG CGC TGG AAC AAT CAT CCC ACA       1548
       Met Asp Gln Gln Phe Cys Leu Arg Trp Asn Asn His Pro Thr
       1                 5                   10
AAT TTG ACC GGC GTG CTA ACC TCA CTG CTG CAG CGG GAG GCG CTA TGC      1596
Asn Leu Thr Gly Val Leu Thr Ser Leu Leu Gln Arg Glu Ala Leu Cys
15              20                  25                  30
GAC GTC ACG CTC GCC TGC GAG GGC GAA ACA GTC AAG GCT CAC CAG ACC      1644
Asp Val Thr Leu Ala Cys Glu Gly Glu Thr Val Lys Ala His Gln Thr
                35                  40                  45
ATC CTG TCA GCC TGC AGT CCG TAC TTC GAG ACG ATT TTC CTA CAG AAC      1692
Ile Leu Ser Ala Cys Ser Pro Tyr Phe Glu Thr Ile Phe Leu Gln Asn
            50                  55                  60
CAG CAT CCA CAT CCC ATC ATC TAC TTG AAA GAT GTC AGA TAC TCA GAG      1740
Gln His Pro His Pro Ile Ile Tyr Leu Lys Asp Val Arg Tyr Ser Glu
        65                  70                  75
ATG CGA TCT CTG CTC GAC TTC ATG TAC AAG GGC GAG GTC AAC GTG GGC      1788
Met Arg Ser Leu Leu Asp Phe Met Tyr Lys Gly Glu Val Asn Val Gly
    80                  85                  90
CAG AGT TCG CTG CCC ATG TTT CTC AAG ACG GCC GAG AGC CTG CAG GTG      1836
Gln Ser Ser Leu Pro Met Phe Leu Lys Thr Ala Glu Ser Leu Gln Val
95                  100                 105                 110
CGT GGT CTC ACA GAT AAC AAC AAT CTG AAC TAC CGC TCC GAC TGC GAC      1884
Arg Gly Leu Thr Asp Asn Asn Asn Leu Asn Tyr Arg Ser Asp Cys Asp
                115                 120                 125
AAG CTG CGC GAT TCG GCG GCC AGT TCG CCG ACC GGA CGT GGG CCG AGT      1932
Lys Leu Arg Asp Ser Ala Ala Ser Ser Pro Thr Gly Arg Gly Pro Ser
            130                 135                 140
AAT TAC ACT GGC GGC CTG GGC GGC GCT GGG GGC GTG GCC GAT GCG ATG      1980
Asn Tyr Thr Gly Gly Leu Gly Gly Ala Gly Gly Val Ala Asp Ala Met
        145                 150                 155
CGC GAA TCC CGC GAC TCC CTG CGC TCC CGC TGC GAA CGG GAT CTG CGC      2028
Arg Glu Ser Arg Asp Ser Leu Arg Ser Arg Cys Glu Arg Asp Leu Arg
    160                 165                 170
```

| | | | | | | | | | | | | | | | | |
|---|---|---|---|---|---|---|---|---|---|---|---|---|---|---|---|---|
| GAC | GAG | CTG | ACG | CAG | CGC | AGC | AGC | AGC | ATG | AGC | GAA | CGC | AGC | TCG | | 2076 |
| Asp | Glu | Leu | Thr | Gln | Arg | Ser | Ser | Ser | Met | Ser | Glu | Arg | Ser | Ser | | |
| 175 | | | | 180 | | | | | 185 | | | | | 190 | | |
| GCG | GCA | GCA | GCG | GCG | GCG | GCG | GCA | GCA | GCA | GCG | GTA | GCG | GCC | GCC | GGC | 2124 |
| Ala | Ala | Ala | Ala | Ala | Ala | Ala | Ala | Ala | Ala | Ala | Val | Ala | Ala | Ala | Gly | |
| | | | | 195 | | | | | 200 | | | | | 205 | | |
| GGC | AAT | GTG | AAT | GCG | GCT | GCC | GTC | GCC | CTG | GGC | CTG | ACC | ACG | CCC | ACC | 2172 |
| Gly | Asn | Val | Asn | Ala | Ala | Ala | Val | Ala | Leu | Gly | Leu | Thr | Thr | Pro | Thr | |
| | | | 210 | | | | | 215 | | | | | 220 | | | |
| GCG | GCG | GCA | GCT | GCG | GCG | GTA | GCA | GCT | GCG | GTG | GCA | GCG | GCC | GCC | AAT | 2220 |
| Ala | Ala | Ala | Ala | Ala | Ala | Val | Ala | Ala | Ala | Val | Ala | Ala | Ala | Ala | Asn | |
| | | | | 225 | | | | | 230 | | | | | 235 | | |
| CGA | AGT | GCC | AGC | GCC | GAT | GGA | TGC | AGC | GAT | CGG | GGA | AGC | GAA | CGC | GGT | 2268 |
| Arg | Ser | Ala | Ser | Ala | Asp | Gly | Cys | Ser | Asp | Arg | Gly | Ser | Glu | Arg | Gly | |
| | | | | 240 | | | | | 245 | | | | | 250 | | |
| ACG | CTC | GAG | CGG | ACG | GAT | AGT | CGC | GAT | GAT | CTA | TTG | CAG | CTG | GAT | TAT | 2316 |
| Thr | Leu | Glu | Arg | Thr | Asp | Ser | Arg | Asp | Asp | Leu | Leu | Gln | Leu | Asp | Tyr | |
| 255 | | | | | 260 | | | | | 265 | | | | | 270 | |
| AGC | AAC | AAG | GAT | AAC | AAC | AAT | AGC | AAC | AGC | AGT | AGT | ACC | GGC | GGC | AAC | 2364 |
| Ser | Asn | Lys | Asp | Asn | Asn | Asn | Ser | Asn | Ser | Ser | Ser | Thr | Gly | Gly | Asn | |
| | | | | 275 | | | | | 280 | | | | | 285 | | |
| AAC | AAC | AAC | AAT | AAT | AAT | AAC | AAC | AAC | AAT | AGC | AGC | AGC | AAC | AAC | AAC | 2412 |
| Asn | Asn | Asn | Asn | Asn | Asn | Asn | Asn | Asn | Asn | Ser | Ser | Ser | Asn | Asn | Asn | |
| | | | | 290 | | | | | 295 | | | | | 300 | | |
| AAC | AGC | AGC | AGC | AAT | AGG | GAG | CGC | AAC | AAT | AGC | GGC | GAA | CGT | GAG | CGG | 2460 |
| Asn | Ser | Ser | Ser | Asn | Arg | Glu | Arg | Asn | Asn | Ser | Gly | Glu | Arg | Glu | Arg | |
| | | | 305 | | | | | 310 | | | | | 315 | | | |
| GAG | CGA | GAA | AGA | GAG | CGT | GAG | CGG | GAC | AGG | GAC | AGG | GAG | CTG | TCC | ACC | 2508 |
| Glu | Arg | Glu | Arg | Glu | Arg | Glu | Arg | Asp | Arg | Asp | Arg | Glu | Leu | Ser | Thr | |
| | | | 320 | | | | | 325 | | | | | 330 | | | |
| ACG | CCG | GTG | GAG | CAG | CTG | AGT | AGT | AGT | AAG | CGC | AGA | CGT | AAG | AAC | TCA | 2556 |
| Thr | Pro | Val | Glu | Gln | Leu | Ser | Ser | Ser | Lys | Arg | Arg | Arg | Lys | Asn | Ser | |
| 335 | | | | | 340 | | | | | 345 | | | | | 350 | |
| TCA | TCC | AAC | TGT | GAT | AAC | TCG | CTG | TCC | TCG | AGC | CAC | CAG | GAC | AGG | CAC | 2604 |
| Ser | Ser | Asn | Cys | Asp | Asn | Ser | Leu | Ser | Ser | Ser | His | Gln | Asp | Arg | His | |
| | | | | 355 | | | | | 360 | | | | | 365 | | |
| TAC | CCG | CAG | GAC | TCT | CAG | GCC | AAC | TTC | AAG | TCG | AGT | CCC | GTG | CCC | AAA | 2652 |
| Tyr | Pro | Gln | Asp | Ser | Gln | Ala | Asn | Phe | Lys | Ser | Ser | Pro | Val | Pro | Lys | |
| | | | 370 | | | | | 375 | | | | | 380 | | | |
| ACG | GGC | GGC | AGC | ACA | TCG | GAA | TCG | GAG | GAC | GCC | GGC | GGT | CGC | CAC | GAC | 2700 |
| Thr | Gly | Gly | Ser | Thr | Ser | Glu | Ser | Glu | Asp | Ala | Gly | Gly | Arg | His | Asp | |
| | | | 385 | | | | | 390 | | | | | 395 | | | |
| TCG | CCG | CTG | TCG | ATG | ACC | ACA | AGC | GTT | CAT | CTG | GGC | GGC | GGT | GGT | GGC | 2748 |
| Ser | Pro | Leu | Ser | Met | Thr | Thr | Ser | Val | His | Leu | Gly | Gly | Gly | Gly | Gly | |
| | | | 400 | | | | | 405 | | | | | 410 | | | |
| AAT | GTG | GGC | GCG | GCC | AGC | GCC | CTT | AGC | GGT | CTG | AGC | CAG | TCG | CTG | AGC | 2796 |
| Asn | Val | Gly | Ala | Ala | Ser | Ala | Leu | Ser | Gly | Leu | Ser | Gln | Ser | Leu | Ser | |
| 415 | | | | | 420 | | | | | 425 | | | | | 430 | |
| ATC | AAG | CAG | GAG | CTG | ATG | GAC | GCC | CAG | CAG | CAG | CAG | CAG | CAT | CGG | GAA | 2844 |
| Ile | Lys | Gln | Glu | Leu | Met | Asp | Ala | Gln | Gln | Gln | Gln | Gln | His | Arg | Glu | |
| | | | | | 435 | | | | | 440 | | | | | 445 | |
| CAC | CAC | GTG | GCC | CTG | CCC | CCA | GAT | TAC | TTG | CCG | AGC | GCC | GCT | CTA | AAG | 2892 |
| His | His | Val | Ala | Leu | Pro | Pro | Asp | Tyr | Leu | Pro | Ser | Ala | Ala | Leu | Lys | |
| | | | 450 | | | | | 455 | | | | | 460 | | | |
| CTG | CAC | GCG | GAG | GAT | ATG | TCA | ACG | CTG | CTC | ACG | CAG | CAT | GCT | TTG | CAA | 2940 |
| Leu | His | Ala | Glu | Asp | Met | Ser | Thr | Leu | Leu | Thr | Gln | His | Ala | Leu | Gln | |
| | | 465 | | | | | 470 | | | | | 475 | | | | |
| GCA | GCA | GAT | GCG | CGG | GAC | GAG | CAC | AAC | GAC | GCC | AAA | CAA | CTG | CAG | CTG | 2988 |
| Ala | Ala | Asp | Ala | Arg | Asp | Glu | His | Asn | Asp | Ala | Lys | Gln | Leu | Gln | Leu | |
| 480 | | | | | 485 | | | | | 490 | | | | | | |

-continued

| | | | | | | | | | | | | | | | | |
|---|---|---|---|---|---|---|---|---|---|---|---|---|---|---|---|---|
| GAC | CAG | ACG | GAC | AAT | ATC | GAC | GGC | AGC | AGC | GCC | CGC | CAC | CAC | CTG | TCG | 3036 |
| Asp | Gln | Thr | Asp | Asn | Ile | Asp | Gly | Ser | Ser | Ala | Arg | His | His | Leu | Ser | |
| 495 | | | | 500 | | | | | 505 | | | | | 510 | | |
| ACC | CCC | CTG | TCG | ACC | TCG | TCG | TCG | GCC | TCG | CCC | CCG | CCG | CCC | CCT | TTC | 3084 |
| Thr | Pro | Leu | Ser | Thr | Ser | Ser | Ser | Ala | Ser | Pro | Pro | Pro | Pro | Pro | Phe | |
| | | | | 515 | | | | | 520 | | | | | 525 | | |
| GGG | ATG | CAC | CTG | TCG | GCG | GCC | CTG | AAA | CGC | GAG | TAC | CAT | CCT | CTG | CAC | 3132 |
| Gly | Met | His | Leu | Ser | Ala | Ala | Leu | Lys | Arg | Glu | Tyr | His | Pro | Leu | His | |
| | | | 530 | | | | | 535 | | | | | 540 | | | |
| TAT | ATG | GCC | GCC | GGC | AAC | GGT | CAC | AAC | GGC | CCA | TCG | GCG | CTT | GGT | TAT | 3180 |
| Tyr | Met | Ala | Ala | Gly | Asn | Gly | His | Asn | Gly | Pro | Ser | Ala | Leu | Gly | Tyr | |
| | | 545 | | | | | 550 | | | | | 555 | | | | |
| GGC | AAT | CAG | GGA | TCG | GGC | AAT | GCG | CCG | AAT | AGT | GCC | GGA | GGA | GCT | GGA | 3228 |
| Gly | Asn | Gln | Gly | Ser | Gly | Asn | Ala | Pro | Asn | Ser | Ala | Gly | Gly | Ala | Gly | |
| | 560 | | | | | 565 | | | | | 570 | | | | | |
| TCG | GTT | GCG | GGC | GGA | GTG | GGA | GCC | GGC | GGA | GGA | GCC | GGC | GGA | GCA | ACT | 3276 |
| Ser | Val | Ala | Gly | Gly | Val | Gly | Ala | Gly | Gly | Ala | Gly | Gly | Ala | Thr | | |
| 575 | | | | | 580 | | | | | 585 | | | | | 590 | |
| GGA | GCA | GCT | GGC | CAT | AAT | TCG | CAT | CAC | ACC | ATG | TCG | TAC | CAC | AAC | ATG | 3324 |
| Gly | Ala | Ala | Gly | His | Asn | Ser | His | His | Thr | Met | Ser | Tyr | His | Asn | Met | |
| | | | | 595 | | | | 600 | | | | | 605 | | | |
| TTC | ACG | CCG | TCC | CGC | GAT | CCG | GGC | ACC | ATG | TGG | CGG | TGC | CGC | TCC | TGC | 3372 |
| Phe | Thr | Pro | Ser | Arg | Asp | Pro | Gly | Thr | Met | Trp | Arg | Cys | Arg | Ser | Cys | |
| | | | 610 | | | | | 615 | | | | | 620 | | | |
| GGC | AAG | GAG | GTG | ACC | AAT | CGC | TGG | CAC | CAC | TTT | CAC | TCC | CAC | ACC | GCC | 3420 |
| Gly | Lys | Glu | Val | Thr | Asn | Arg | Trp | His | His | Phe | His | Ser | His | Thr | Ala | |
| | | 625 | | | | | 630 | | | | | 635 | | | | |
| CAG | CGG | TCC | ATG | TGT | CCC | TAC | TGC | CCG | GCC | ACC | TAC | AGC | AGG | ATC | GAT | 3468 |
| Gln | Arg | Ser | Met | Cys | Pro | Tyr | Cys | Pro | Ala | Thr | Tyr | Ser | Arg | Ile | Asp | |
| | 640 | | | | | 645 | | | | | 650 | | | | | |
| ACG | CTG | CGC | TCC | CAT | TTG | CGG | GTG | AAG | CAT | CCG | GAT | CGC | CTG | CTC | AAG | 3516 |
| Thr | Leu | Arg | Ser | His | Leu | Arg | Val | Lys | His | Pro | Asp | Arg | Leu | Leu | Lys | |
| 655 | | | | | 660 | | | | | 665 | | | | | 670 | |
| CTG | AAC | TCG | TCC | ATT | TAAGGGCGTG | GCCGGGGCCC | AAGTGCAGCC | CATCACCGCC | | | | | | | | 3571 |
| Leu | Asn | Ser | Ser | Ile | | | | | | | | | | | | |
| | | | | 675 | | | | | | | | | | | | |

| | | | | | |
|---|---|---|---|---|---|
| AGCTTTACCA | GCAGCAACAA | CAGCCGCATC | ATAAGCAGAA | GCAGAAGCAG | CAACAGCAGC | 3631 |
| AGCAGCAACA | GCAGCAGCAT | CAGCCGCATC | AGCAGCAACA | GCAACCAGCT | TACTACGTCA | 3691 |
| GCAACTATAG | CAACTACAGC | AATAATAGAT | ACAGCTACAG | CGATAGTTTA | TTGTAAATCG | 3751 |
| CTGCAGTTCT | AGGTGGATTT | TTCTTGCATT | TAGTCGTCGT | CCAGTCGTGT | ACATTACCCA | 3811 |
| CTAGCTATCC | AAGCAATAAC | CATAACCCAA | ACTAGTAGAA | AACCGAAGAT | GCTATGCTAT | 3871 |
| GGCAAAACGT | AAAGCGTTAA | ACACAAGTAT | ATTGATAATC | TTAACTAAAC | TTATTGATAA | 3931 |
| ACTTTGACAC | AATCGTCCCA | TCAATTTATA | AATGTGTATA | ACTAAGGAAG | ATTAGGAAAA | 3991 |
| GGTTTCAGTT | GCGAGTCGAG | GAGAAGGATA | TGCCCAGCAT | AGAGGGCCAG | TGGAGGCGGA | 4051 |
| AAAAAAGTTT | TCCAAAGCCA | CAACAAACCG | TTTCGAAGGT | TTCTAAATGT | TGTTTCCTAA | 4111 |
| AAACTATAAA | GTAATAACTA | CACTAATACT | AGAGAGAGAA | AGTCGAGGAG | AATCGTTTTG | 4171 |
| AGCCGATTCA | GCAAATTGGG | GTCACTACCA | CATCACGCGG | GGTCACCAGC | AGCAGCAGCA | 4231 |
| GCAGCAGCAA | ATGGAGGATG | CGGATGCGAA | TGCGGATGCG | GATGAGGATC | AGGATGAGGA | 4291 |
| TCAGCCAGCA | CAGCAACAGT | CACCCACAAA | TACTACTCAT | ACGAAGGTCA | CATTAGGTTT | 4351 |
| TAGTTTACTT | TAATTTGTAA | TGTCTAGATT | TTAGTGTTAA | CCGATATGTT | CTGCGGAGTA | 4411 |
| GGAAACGGAT | GAGGGCTACT | CAACCAACTA | CAAAGAAATT | TCATATACC | TCAAATGCAT | 4471 |
| TTCAGTTTTA | TTGTTGATTG | CTTTAATTTT | AGTCTACGTA | GTCAGTTAGC | ACTTATACAT | 4531 |

```
AAAGTACCAC ATACATATAT GTTATTTTTT AATCGGTTCC AATTTGAATC GGCGAGATAG    4591

CCAATAGTTT ACCAATGTTT TCCTCTGTTT TTTAGTGTGT GTGGTGTGTT CCCTATCACT    4651

ATCACACTTT TGATTTTGTC CTATGCGTTA AGTTGAAGAT TTAGGATTA GCTCGAACCA    4711

CTTGAACCAC CTCACTTTTT TTTGTTAAGC TTGTTTATAT TTTATATTTA TGGTCACACG    4771

TTTATTTAGT TAAAGTACAC TAAACACATA TGAAATCACG CGGAAGAAAG TTAGTTGATA    4831

TGAG                                                                 4835
```

( 2 ) INFORMATION FOR SEQ ID NO:10:

( i ) SEQUENCE CHARACTERISTICS:
        ( A ) LENGTH: 675 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Asp Gln Gln Phe Cys Leu Arg Trp Asn Asn His Pro Thr Asn Leu
 1               5                  10                  15

Thr Gly Val Leu Thr Ser Leu Leu Gln Arg Glu Ala Leu Cys Asp Val
            20                  25                  30

Thr Leu Ala Cys Glu Gly Glu Thr Val Lys Ala His Gln Thr Ile Leu
        35                  40                  45

Ser Ala Cys Ser Pro Tyr Phe Glu Thr Ile Phe Leu Gln Asn Gln His
    50                  55                  60

Pro His Pro Ile Ile Tyr Leu Lys Asp Val Arg Tyr Ser Glu Met Arg
65                  70                  75                  80

Ser Leu Leu Asp Phe Met Tyr Lys Gly Glu Val Asn Val Gly Gln Ser
                85                  90                  95

Ser Leu Pro Met Phe Leu Lys Thr Ala Glu Ser Leu Gln Val Arg Gly
            100                 105                 110

Leu Thr Asp Asn Asn Asn Leu Asn Tyr Arg Ser Asp Cys Asp Lys Leu
        115                 120                 125

Arg Asp Ser Ala Ala Ser Ser Pro Thr Gly Arg Gly Pro Ser Asn Tyr
    130                 135                 140

Thr Gly Gly Leu Gly Gly Ala Gly Gly Val Ala Asp Ala Met Arg Glu
145                 150                 155                 160

Ser Arg Asp Ser Leu Arg Ser Arg Cys Glu Arg Asp Leu Arg Asp Glu
                165                 170                 175

Leu Thr Gln Arg Ser Ser Ser Ser Met Ser Glu Arg Ser Ser Ala Ala
            180                 185                 190

Ala Ala Ala Ala Ala Ala Ala Ala Val Ala Ala Ala Gly Gly Asn
        195                 200                 205

Val Asn Ala Ala Ala Val Ala Leu Gly Leu Thr Thr Pro Thr Ala Ala
    210                 215                 220

Ala Ala Ala Ala Val Ala Ala Ala Val Ala Ala Ala Asn Arg Ser
225                 230                 235                 240

Ala Ser Ala Asp Gly Cys Ser Asp Arg Gly Ser Glu Arg Gly Thr Leu
                245                 250                 255

Glu Arg Thr Asp Ser Arg Asp Asp Leu Leu Gln Leu Asp Tyr Ser Asn
            260                 265                 270

Lys Asp Asn Asn Asn Ser Asn Ser Ser Thr Gly Gly Asn Asn Asn
        275                 280                 285

Asn Asn Asn Asn Asn Asn Asn Asn Ser Ser Ser Asn Asn Asn Asn Ser
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 290 |     |     |     |     | 295 |     |     |     |     | 300 |
| Ser<br>305 | Ser | Asn | Arg | Glu | Arg<br>310 | Asn | Asn | Ser | Gly | Glu<br>315 | Arg | Glu | Arg | Glu | Arg<br>320 |
| Glu | Arg | Glu | Arg | Glu<br>325 | Arg | Asp | Arg | Asp<br>330 | Arg | Glu | Leu | Ser | Thr | Thr<br>335 | Pro |
| Val | Glu | Gln | Leu<br>340 | Ser | Ser | Ser | Lys | Arg<br>345 | Arg | Arg | Lys | Asn | Ser<br>350 | Ser | Ser |
| Asn | Cys | Asp<br>355 | Asn | Ser | Leu | Ser | Ser<br>360 | Ser | His | Gln | Asp | Arg<br>365 | His | Tyr | Pro |
| Gln | Asp<br>370 | Ser | Gln | Ala | Asn | Phe<br>375 | Lys | Ser | Ser | Pro | Val<br>380 | Pro | Lys | Thr | Gly |
| Gly<br>385 | Ser | Thr | Ser | Glu | Ser<br>390 | Glu | Asp | Ala | Gly | Gly<br>395 | Arg | His | Asp | Ser | Pro<br>400 |
| Leu | Ser | Met | Thr | Thr<br>405 | Ser | Val | His | Leu | Gly<br>410 | Gly | Gly | Gly | Gly | Asn<br>415 | Val |
| Gly | Ala | Ala | Ser<br>420 | Ala | Leu | Ser | Gly | Leu<br>425 | Ser | Gln | Ser | Leu | Ser<br>430 | Ile | Lys |
| Gln | Glu | Leu<br>435 | Met | Asp | Ala | Gln | Gln<br>440 | Gln | Gln | Gln | His | Arg<br>445 | Glu | His | His |
| Val | Ala<br>450 | Leu | Pro | Pro | Asp | Tyr<br>455 | Leu | Pro | Ser | Ala | Ala<br>460 | Leu | Lys | Leu | His |
| Ala<br>465 | Glu | Asp | Met | Ser | Thr<br>470 | Leu | Leu | Thr | Gln | His<br>475 | Ala | Leu | Gln | Ala | Ala<br>480 |
| Asp | Ala | Arg | Asp | Glu<br>485 | His | Asn | Asp | Ala | Lys<br>490 | Gln | Leu | Gln | Leu | Asp<br>495 | Gln |
| Thr | Asp | Asn | Ile<br>500 | Asp | Gly | Ser | Ser | Ala<br>505 | Arg | His | His | Leu | Ser<br>510 | Thr | Pro |
| Leu | Ser | Thr<br>515 | Ser | Ser | Ser | Ala | Ser<br>520 | Pro | Pro | Pro | Pro | Phe<br>525 | Gly | Met |
| His | Leu<br>530 | Ser | Ala | Ala | Leu | Lys<br>535 | Arg | Glu | Tyr | His | Pro<br>540 | Leu | His | Tyr | Met |
| Ala<br>545 | Ala | Gly | Asn | Gly | His<br>550 | Asn | Gly | Pro | Ser | Ala<br>555 | Leu | Gly | Tyr | Gly | Asn<br>560 |
| Gln | Gly | Ser | Gly | Asn<br>565 | Ala | Pro | Asn | Ser | Ala<br>570 | Gly | Gly | Ala | Gly | Ser<br>575 | Val |
| Ala | Gly | Gly | Val<br>580 | Gly | Ala | Gly | Gly | Gly<br>585 | Ala | Gly | Gly | Ala | Thr<br>590 | Gly | Ala |
| Ala | Gly | His<br>595 | Asn | Ser | His | His | Thr<br>600 | Met | Ser | Tyr | His | Asn<br>605 | Met | Phe | Thr |
| Pro | Ser<br>610 | Arg | Asp | Pro | Gly | Thr<br>615 | Met | Trp | Arg | Cys | Arg<br>620 | Ser | Cys | Gly | Lys |
| Glu<br>625 | Val | Thr | Asn | Arg | Trp<br>630 | His | His | Phe | His | Ser<br>635 | His | Thr | Ala | Gln | Arg<br>640 |
| Ser | Met | Cys | Pro | Tyr<br>645 | Cys | Pro | Ala | Thr | Tyr<br>650 | Ser | Arg | Ile | Asp | Thr<br>655 | Leu |
| Arg | Ser | His | Leu<br>660 | Arg | Val | Lys | His | Pro<br>665 | Asp | Arg | Leu | Leu | Lys<br>670 | Leu | Asn |
| Ser | Ser | Ile<br>675 |

( 2 ) INFORMATION FOR SEQ ID NO:11:

( i ) SEQUENCE CHARACTERISTICS:
( A ) LENGTH: 608 base pairs
( B ) TYPE: nucleic acid ( C ) STRANDEDNESS: double
( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
    ( C ) INDIVIDUAL ISOLATE: EcoRI genomic clone
        containing 3 dsx repeats ( i x ) FEATURE:
    ( A ) NAME/KEY: misc_feature
    ( B ) LOCATION: 324..420
    ( D ) OTHER INFORMATION: /note= "where N has not
        been precisely determined"

( i x ) FEATURE:
    ( A ) NAME/KEY: misc_feature
    ( B ) LOCATION: 483..485
    ( D ) OTHER INFORMATION: /note= "where N has not
        been precisely determined"

( i x ) FEATURE:
    ( A ) NAME/KEY: misc_feature
    ( B ) LOCATION: 509..509
    ( D ) OTHER INFORMATION: /note= "where N has not
        been precisely determined"

( x i ) SEQUENCE DESCRIPTION: SEQ ID NO:11:

```
GAATTCGAGG  ACGTGTGACG  ATGGAGCAAC  CCTTCCCCCC  CAGATCGAAA  GAGAATATCA     60
TCAATCAACA  TTCCCGTGCC  CGGAGGAGCG  GCTCTTCAAT  CAACACTCAA  CCCGAACTGG    120
GCCCTCAAAA  GCCCGGCAAC  CTAAAGTTAG  TCTTTCATTA  GCCTCTTCTA  TCAATTAGGT    180
AGTCAGCCAA  CGTTTCTCTC  TCTCTCATAA  TTCTAACCGA  AAGTAAGCAT  AGAAAAGAAC    240
CAATACTTCA  ATCAACATAC  CCACAAAAAA  AAACAAATCC  CCACCAACTG  GCGTCGGTAA    300
GTGAAGAGCC  ATTTTAATTA  TAGNNNNNNN  NNNNNNNNNN  NNNNNNNNNN  NNNNNNNNNN    360
NNNNNNNNNN  NNNNNNNNNN  NNNNNNNNNN  NNNNNNNNNN  NNNNNNNNNN  NNNNNNNNNN    420
TGATCGCCGA  TGATGCATGT  GATAAGCAAG  TGATGAACAA  TCCGTAGCAA  TCAGGCAGTA    480
GGNNNCTTGA  ACAAATTTAA  CTTAGCTGNA  TTTTGCGCAT  GCCAAATGAA  AAATAACAAA    540
CCGTAAATTC  CAATGGTAAC  TAAAACTAGC  AATACTAACT  CTAGCCGATG  GAACATGCAA    600
CCGAATTC                                                                  608
```